(12) United States Patent
Lin et al.

(10) Patent No.: US 9,750,791 B2
(45) Date of Patent: Sep. 5, 2017

(54) **ANTI-*MYCOPLASMA* SPP. SUBUNIT VACCINE**

(71) Applicant: AGRICULTURAL TECHNOLOGY RESEARCH INSTITUTE, Hsinchu (TW)

(72) Inventors: Jiunn-Horng Lin, Miaoli County (TW); Jyh-Perng Wang, Miaoli County (TW); Ming-Wei Hsieh, Miaoli County (TW); Zeng-Weng Chen, Miaoli County (TW); Chien-Yu Fang, Miaoli County (TW); Hsueh-Tao Liu, Miaoli County (TW); Ping-Cheng Yang, Miaoli County (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/453,660

(22) Filed: Mar. 8, 2017

(65) Prior Publication Data
US 2017/0182143 A1    Jun. 29, 2017

Related U.S. Application Data

(62) Division of application No. 15/383,962, filed on Dec. 19, 2016, which is a division of application No. 14/765,512, filed as application No. PCT/CN2013/071379 on Feb. 5, 2013, now Pat. No. 9,561,267.

(51) Int. Cl.
*A61K 39/02*      (2006.01)
*A61K 39/385*     (2006.01)
*A61K 39/00*      (2006.01)

(52) U.S. Cl.
CPC .... *A61K 39/0241* (2013.01); *A61K 2039/552* (2013.01); *A61K 2039/55505* (2013.01)

(58) Field of Classification Search
None
See application file for complete search history.

(56) References Cited

U.S. PATENT DOCUMENTS

2006/0233823 A1   10/2006  King et al.
2009/0280535 A1   11/2009  Wang

FOREIGN PATENT DOCUMENTS

| CN | 1296953 A     | 5/2001  |
| EP | 0359919 A2    | 3/1990  |
| TW | 200951219 A1  | 12/2009 |

OTHER PUBLICATIONS

"ABC transporter xylose-binding lipoprotein," NCBI Database, accession No. YP_287990, Nov. 2, 2010, one page.
"Hypothetical protein mhp389," NCBI Database, accession No. YP_115900, Dec. 21, 2012, one page.
"Hypothetical protein mhp683," NCBI Database, accession No. YP_116191, Dec. 21, 2012, one page.
"Lipoprotein," NCBI Database, accession No. YP_115889, Dec. 21, 2012, one page.
"Periplasmic sugar-binding proteins," NCBI Database, accession No. YP_15659, Dec. 21, 2012, one page.
"Pyruvate dehydrogenase E1-subunit alpha," NCBI Database, accession No. YP_115778, Dec. 21, 2012, one page.
Butt at al., "Mycoplasma Genitalium: A Comparative Genomics Study of Metabolic Pathways for the Identification of Drug and Vaccine Targets," Infection, Genetics and Evolution. vol. 12, 2012 (Available Online Oct. 25, 2011), pp. 53-62.
English translation of the International Preliminary Report on Patentability (Form PCT/IPEA/409), dated Aug. 5, 2015, for International Application No. PCT/CN2013/071379.
Liu at al., J. Bacteriol. Feb. 2011, vol. 193, No. 4, pp. 1016-1017.
Minion et al., J. Bacteriol. Nov. 2004, vol. 186 No. 21, pp. 7123-7133.
Uniprot Database, "Periplasmic Sugar-binding Protein, rbsB, MHP7448_0234, Mycoplasma Hyopneumoniae (strain 7448)," Q4A8D1, Sep. 13, 2005—v1, pp. 1-4 (Total 2 pages).
Uniprot Database, "Putative D-ribose-binding Protein Mutant, mhp145, Mycoplasma Hyopneumoniae (strain 232)," Q601Q6, Nov. 23, 2004—v1, pp. 1-4 (Total 2 pages).
Uniprot Database, "Putative Lipoprotein, mhp378, Mycoplasma Hyopneumoniae (strain 232)," Q600S6, Nov. 23, 2004—v1, pp. 1-4 (Total 2 pages).
Uniprot Database, "Pyruvate Dehydrogenase E1-alpha Subunit, pdhA, MHP168_186, Mycoplasma Hyopneumoniae (strain 168)," E4QSJ1, Feb. 8, 2011—v1, pp. 1-4 (Total 2 pages).
Uniprot Database, "Uncharacterized Protein, mhp389, Mycoplasma Hyopneumoniae (strain 232)," Q600R5, Nov. 23, 2004—v1, pp. 1-4 (Total 2 pages).

(Continued)

*Primary Examiner* — Jennifer Graser
(74) *Attorney, Agent, or Firm* — Birch, Stewart, Kolasch & Birch, LLP

(57) ABSTRACT

Provided in the present invention are anti-*Mycoplasma* spp. subunit vaccines, especially proteins suitable for being used as the active ingredient of the *Mycoplasma* spp. subunit vaccines, and a vaccine prepared therefrom. Upon experimenting, it is confirmed that the proteins can elicit an immune response having sufficient strength to avoid the infection of *Mycoplasma* spp. in pigs. The vaccine can comprise one of the aforementioned proteins as an active ingredient, or can comprise two or more of the proteins to form a form of cocktail vaccine. The vaccine of the present invention is not only more safe than conventional vaccines, but also has equivalent or even better immune effects.

5 Claims, 6 Drawing Sheets
(6 of 6 Drawing Sheet(s) Filed in Color)

(56) References Cited

OTHER PUBLICATIONS

Uniprot Database, "Uncharacterized Protein, mhp683, Mycoplasma Hyopneumoniae (strain 232)," Q5ZZM4, Nov. 23, 2004—v1, pp. 1-4 (Total 2 pages).
Uniprotkb Database, "ABC Transporter Xylose-binding Lipoprotein, xyLF, MHP7448_0604, Mycoplasma Hyopneumoniae (strain 7448)," Q4A7C2, May 15, 2007—v2, pp. 1-4 (Total 2 pages).
Vaconcelos et al., J. Bacteriol. Aug. 2005, vol. 187, No. 16, pp. 5568-5577.
Xu Jian et al., "Cloning and Expression of Pyruvate Dehydrogenase E1-α Subunit Gene(pdha) in Mycoplasma Ovipneumoniae and its Immunologic Activity Evaluation," Journal of Agricultural Biotechnology, Mar. 2012, vol. 20

| Antigen(s) | Score | Lung, Dorsal | Lung, Ventral |
|---|---|---|---|
| XylF+Mhp145 | 13 |  |  |
| PdhA+P78 | 15 |  |  |
| P132 | 26 |  |  |
| XylF | 27 |  |  |

| Antigen(s) | Score | Lung, Dorsal | Lung, Ventral |
|---|---|---|---|
| Mhp145 | 28 |  |  |
| P78 | 25 |  |  |
| PdhA | 28 |  |  |
| EutD | 24 |  |  |

| Antigen(s) | Score | Lung, Dorsal | Lung, Ventral |
|---|---|---|---|
| Mhp389 | 27 |  |  |
| *Vaccine PRIT-5* (positive control) | 20 |  |  |
| *Un-treated control* | 43 |  |  |

SEQUENCE LISTING

```
<160> NUMBER OF SEQ ID NOS: 100

<210> SEQ ID NO 1
<211> LENGTH: 1125
<212> TYPE: DNA
<213> ORGANISM: Artificial Sequence
<220> FEATURE:
<223> OTHER INFORMATION: mutated pdhA gene

<400> SEQUENCE: 1
atggacaaat ttcgctatgt aaagcctggt caaattatgg caaaagatga agaaatgatt      60
cgctttcttg atattgatgg taatctttta tcttcaactg ttttttggacc aatcgacgaa    120 acaaatgata ttcgcttatc aaaacaggaa atcaaaaaag cttatgaatt tatggtttta    180
tctcgccaac aagatacgta tatgacacaa ctacagcgac aaggtagaat gttgactttt    240
gcccctaact ttggtgaaga agctcttcaa gtagcctcag ggatggcgct aacaaaagat    300
gactggtttg tcccagcttt tcgttcaaat gcaacaatgt tatatcttgg cgtgccaatg    360
atcttgcaaa tgcaatattg gaatggtagc gaaaaaggta atgtaattcc cgaaaatgtt    420
aatgttttac ctattaacat tcccatcgga acgcagtttt cccatgctgc cggaattgct    480
tatgcagcaa aactaacagg taaaaaaata gtttcaatga gttttattgg aaacggggga    540
actgccgaag gcgagtttta cgaggcgcta aatattgcaa gtatttggaa atgaccagtt    600
gttttttgcg taaataacaa tcaatgggca atttcaaccc caaataaata tgaaaacggt    660
gcctcaacaa ttgctgcaaa agcaatggca gccggaattc ctggaattcg tgtagacgga    720
aatgaccttt tagcttctta tgaagtaatc aaggaagctg ttgattatgc tcgttctgga    780
aacggtcctg ttcttgttga gtttgtaact tggcgtcaag gtgttcatac ctcttctgat    840
aatccacgaa tttatcgtac tgttgaagag gaaagagaac acgaaaaatg ggaaccaatg    900
caccggattg aaaaatatat gtttgaccgc ggaattcttg attctgccga aaacaaaaa     960 atttgggatg aagcgcttgc gattgtcaaa gaaacttatg aaaaatctct tgttgggctt   1020
gagtcaacaa ttgatgaaat tttcgatcat acctacaagg ttttaccacc agaacttgaa   1080
gaacaaaaac aagaagcgct tgaattttt aaaggagtaa ataa                     1125
```

<210> SEQ ID NO 2
<211> LENGTH: 1344
<212> TYPE: DNA
<213> ORGANISM: Artificial Sequence
<220> FEATURE:
<223> OTHER INFORMATION: mutated xylF gene

<400> SEQUENCE: 2

```
atgaaatgga ataaatttct tggcttaggc ttagtttttc cgctttcagc aatcgcgaca      60
atctctgccg gatgttggga taagaaaca actaagaag aaaaatcagc cgataatcaa      120
aataaacaaa tcactgatgt ctcaaaaatt tcaggactag ttaatgagcg aaaatccgaa     180
attatggccg caaaagctga tgcaaacaaa cattttgggc taaatatggc aattgtaacc     240
gctgatggaa cggtaaatga taattcattt aaccaatcaa gttgggaggc aattcaacaa     300
cttggcgctc ttactggagg tgagattact tcagtagata gttcaactgc tgaacttgaa     360
ggaaaatata gctcacttgc taataccaac aaaaatgttt gggtactttc tggttttcaa     420
cacggtgatg cgatcacaaa atggttaaaa tccctgaaa ataagcaatt atttactgaa      480
aaaaatatta tcatactcgg aattgactgg actgatactg aaaatgtaat tccaacaggt     540
cgatatatta atttaaccta taaaactgaa gaagccggat ggcttgcagg atatgcgaat     600
gcttccttt tggcaaaaaa attcccaagt gatccaacta aagatcagc aattgttatc       660
ggtggtggga ttttcccagc tgtaactgat tttatcgctg ttatctagc cggaattaaa      720
gcttggaatc taaaaaattc tgataaaaaa acaagataa caactgataa aatcgaaata      780
aatcttgggt tgattttca aaatacttca acaaagaaa gacttgaaca aattgcttca       840
aaagataaac cttcaacact attagcagtc gctggaccac ttactgaaat tttctcggat     900
ataatcgcaa accaaaatga tcgttatctc attggtgttg acaccgacca atcacttgtt     960
tatacaaaaa ctaaaaataa atttttcacc tcaatttga aaaatttagg ttactccgtt     1020
ttcagtgttc ttagtgattt atataccaaa aaatcaaatt caagaaattt agccggcttt    1080
gaatttggta aaaaagtgc aaccgtttat cttggaatta agacaagtt tgtcgatatt      1140
gctgatactt ctttagaagg aaatgataaa aaactcgcaa ctgaagccat ttctgaagct    1200
aaaaagaat ttgaagaaaa aactaagaca actcctgccg aagaagttcg taaaacttta     1260
gaaattccgg aaatgactga taacaacct gataaacaac aggaaagctt agacaaacta      1320
attaccgata ttaataaaaa ttaa                                           1344
```

<210> SEQ ID NO 3
<211> LENGTH: 1122
<212> TYPE: DNA
<213> ORGANISM: Mycoplasma hyopneumoniae

<400> SEQUENCE: 3

```
atagcttcaa ggtcgaatac aactgccaaa gttgccccag ttg

```
gctcaagggt ttattgaaac agttaaaaat ctaaataatc aagcaataaa atacaacctt    540
ttttcttatg gaaatacgg aaaagaaaat gcaaatggaa aaacttacat cggaagacaa    600
gctgatgata atcgcgatct agcaaatcaa agagttgcaa atgatgcaac gcaagtattc    660
caagatgctc aaaaaaggcc acttttggtt tttgggacta atgatgaagc tgccttaggt    720
tcaatttctg cccttgaaag tgcccagatt ccattaggag gtggagataa attccttcca    780
ggttcaggaa aagtttatat taccggagtt gattatacaa atgatgctca aaaagcggta    840
ttaaataata aattatcagc aactgttgaa caagatactg atcttttagg aagactttct    900
ttaataattg cagaaaaaat tcttaaagat caatggaaaa caagtaaata ttctgatttt    960
tattcacaat ttcctcagct tgataaagac aaaaatcctg atgatcaagt tgagcaagga    1020
tattatttta aagtaggaac aaaacttttc tggaaaggac cagatggaaa aggtgaaaaa    1080
cttcaagccg atgaaaatgg gatactccaa aaggtaaatt aa    1122
```

<210> SEQ ID NO 4
<211> LENGTH: 1122
<212> TYPE: DNA
<213> ORGANISM: Artificial Sequence
<220> FEATURE:
<223> OTHER INFORMATION: mutated mhp145 gene

<400> SEQUENCE: 4

```
atagcttcaa ggtcgaatac aactgccaaa gttgccccag ttgctgttgt tttctcaaca    60
agaaataatc cttttttcca aaatgttgaa aaagggattg aaacagcggc aaaagaatta    120 ggagttgact

```
<400> SEQUENCE: 5
ttatcctata aatttaggcg ttttttccta accagcgcac ttagttttgc tcccttggct      60
ttagttgcaa gttgtgttaa taattcccga tttgattcaa atgaggataa taaattagtt     120
tttggtcata cttttttcatc ttcaggaaaa gaggcaaaag cacttgagaa aattattgaa    180
gtctggaata aaactgcaac taatcaaaaa gattttatca aaatggaagc acaatatttc    240
cagaatggct ataatggatc agcggcttca attacaaact ttttacagac aaaagatcgg    300
ataaaactgc aaatattgt cacaaattat ccttcacttc tggcaatagt taataaatat    360
tcaatgactt ttccgcttgt taaagatttt agttctaatc aagaaccaca agatgaaaat    420
gaaaagcaa taaaaagtt cctaaaagag caaggaattt ctgatttcct tgagattaat     480
aaagaagttc ctttccttga tacaaaggga gtttataccc ttccatttgg aaaatcaact    540
gaagttctta caattaataa agttttgttt ggttggatga ttaataaagc acttgctgat    600
ccaaaaaagc cagcaaaaat taagaagaa gataaaccct attttgccga atttcaaaaa    660
ttaggcaagg aaaaaactgg tgatattaaa gaaattgaaa gaatctggaa aaaatatgtc    720
tccgatgatc aaggacttgc aggctatgaa tttcgccgat ccgatcttga aaattttact    780
gacctacaga aattatcatc acgaattctt cgttcttttc cagaggccct ttcaggaggc    840
tccactgatt cggcaaaatc agttttagga attgataatc aagcaacgct agttttgct    900
cttgccagat cagtttcaga aggtaatcga tcccaggaag ttactgttct tgataggcaa    960
aagaatttaa ttgattatat atctttttata gataaacctg attcaattag atataaaaat   1020
ttagaaaaaaa ttttttaattt attaagccaa gggataaaag atcgctcaat ttattataca  1080
tctgcagggg agtataattc aacttttttc cggaatcatc agcaggttt ctcaattggt    1140
tcaacttcag gctatttcca taattttgtc aaaccaacag cgacaaatta tcaaatcgga   1200
tttaagaaaa atgatggtct taagtcagtt tatagcgtta gctatcccaa atttagcgca   1260
attgtatcac ttgaagatct caaggatata accaagatc tagaaataac agcaaccgat    1320
ggtagctcta aattaaaaat tgatgctaaa ttttttaggaa aactcaaaga atatgcacag   1380
caaaatccag ttaaaaaagt gtttatttt actgatcgat cagaaaaacc ttcaggtatc   1440
ttcgaaaaag attatattgt tttaggcaaa tacaaaaatg ataaaaatga agaatttaat    1500
ggccttgtaa ttccaactta tacagaactc tataaaaatt ctggatcaaa tgcccttaat   1560
gatgatgaac ttgcacttga agccccaccg cataaattcg atgcaaatag taaaatcacc   1620
cccattgtcg cccaaggtcc tgatctaatt tttattcatt caactgaaaa agaagataaa   1680
gccgcaaaag cttttgttaa atggcttttg acagaaaaaa tagtctttga ggaaaatagt   1740
caggaaaaaa tgactccgct tgagtatttt gccagagcaa cctcatattt attgccaata   1800
aaatcaacgc ttgataaaac ccattttagt ccaaaaata gatctcagaa attcatactt   1860
gaccaattta gtaaatttct taatgctgat tcaaaggaa aatattcgct tgtctatgat   1920
aatgccgatg caaatgcttc atccttccgt gaatcactag attcttcagt tgcccagatg   1980
caatcattaa aagccagcga tggaaaacta cgtagttta aagagttttt agaaaaacta   2040
gagggaaatt taggtcctgc ttttaaatca aaataa                              2076
```

<210> SEQ ID NO 6
<211> LENGTH: 3549
<212> TYPE: DNA
<213> ORGANISM: Artificial Sequence
<220> FEATURE:
<223> OTHER INFORMATION: mutated P132 gene

<400> SEQUENCE: 6

```
attggactaa caattttttga gaaatcattt agttcccaag tttcaggagg ggtcgataag      60
aacaaagttg tggatttaaa atcagattca gatcaaatct tctcagaaga agattttata     120
agagcagttg agaatcttaa acttttttgat aaatataaac atctaacagc aagaatggca     180
ttaggacttg ctagggaagc agctaatgcc tttaactttt tagatactta tgactacacc     240
ccaattacaa acattcatt taagatttct ttggatattt ccgatgcctt tgcggctaat     300
aaagaagtaa aagcggtagt ggttagtgca tattcccaaa aatatcaagt tacctattca     360
agactaactt ctctaaaagg ttggaaagaa gaagatgatt ttggcgatga tattatagat     420
tatcaaatta atcaagagct ttcaggtcta tcactttctt ccttagcccc tgaaagcgcg     480
catcttttag cctcagaaat ggcttttcgg cttgataatg actttcaagt tgcatataaa     540
aaaacaggat caagagccga ggcttttcgt caggccttga taaagaatta tcttggttat     600
aacttagtta accgccaagg tttgcccact atgctccaaa agggttatgt gctagccccc     660
aaaacaattg aaaataaaaa tgcaagcgaa gaaaaattag taaatataaa tgaaaatgac     720
cgtgcaaggg ttaataaact acaaaaagta gaaaatctag cctttaaaaa cttaagtgat     780
ccaaatggaa cgcttctat tacttttgaa ctctgggacc caaatggtaa attagtatcc     840
gaatacgatt ttaaaattaa gggaatcaaa aaacttgatt ttgatcttaa aaaacaagag     900
gaaaagtac ttcaaaaagt aactgaattt gttgagatta aaccttatgt tcaattaggt     960
ttaatccgtg ataatttatc attgtctgaa attatctata aaaatgataa taatccggag    1020
tatcttagga aaatattagc taaactaaaa gaacacaata acaacaaaag ggtggataat    1080
aatacatcca ctactaaatt tcaagaagag gatcttaaaa acgaaccaaa ttctaatgga    1140
tcagaacaag attctttcga gaaagcaaag gaaaatttcc ttagtttttt tgatctaagg    1200
tcgagactaa ttcctattcc cgatcttcct ttatattatc ttaaagttaa ttcaattaat    1260
tttgatagaa atattgaaga aaatgaaaaa gaaaaattat taaaaaatga acaagtagta    1320
ctcaaagtag attttagtct taaaaaagtt gttagcgata ttagagctcc ttacctagtt    1380
tctagtcagg ttagatcaaa ttatcccccg gttttaaaag cttcgctagc aaaaataggt    1440
aaggggtcaa attcaaaagt tgtccttttta gatcttggaa atttatcttc aagatttaaa    1500
gttcaacttg attatagtgc aaaacaaaga gaaataatta atactttatt aaaggaaaat    1560
ccagaaagag aaaaagaatt acaagctaaa attgaaagta agacgtttag tccaatagat    1620
cttaacaatg atgatctatt agcaatcgaa tttcaatatg aggataaccc tgaaggagat    1680
tggataactt tagggagaat ggaaaagtta gtcaaagagg ttatccaata taaaaaagaa    1740
ggtaaaacct tcttagatga tgaagtcgcg aaaacacttt attatttaga tttccatcat    1800
ctacctcaaa gtaaaaaaga cctcgaagaa tataaagaaa acacaaaaaa caagtttatc    1860
agcgaaataa aacctgctac accagcaagt caagcaaaaa caagtcaagc aaaaaatgaa    1920
aaagaagtaa aacctgaatc agcccaagca gaagcttcat cttcaaattc taatgattct    1980
agtagtaaaa ccacttcttc ttcaagtatg gcgggtacaa cccaaaataa atctacagaa    2040
actccaaatt caagttcaaa ttcaacacca acaagttcag caacaacttc agcaacaact    2100
tcaacaacaa gttcaaattc aagttcaaca acaagttcaa caacaacaac aacttcaaca    2160
caagcagcaa caacttcagc ctcttcggct aaagtaaaaa aactaaatt ccaagaacaa    2220
gtaaaagaac aagaacaaaa acaagaaaaa gcaaagaaa ctaaccaatt attagatact    2280
```

```
aaaagaaata aagaagactc agggcttgga ttaattcttt gggatttcct agtaaattca    2340
aaatataaaa ctctaccagg aactacctgg gatttccatg ttgaaccaga taatttcaat    2400
gatcgtctaa aaataacagc gattctaaaa gaaaatacat cccaggcaaa gtcaaaccca    2460
gatagtaaaa acctaacttc cctatcacga aaccttataa taaaagggt tatggctaat    2520 aaatacattg actacttagt ccaagaagat ccagtacttc ttgtagatta tacaagaaga    2580
aaccagatta aaaccgaaag agaaggacaa ctaatttgga gccagttagc ttcccctcaa    2640
atggcatctc ctgaatctag tcccgaaaag gctaagctcg agatcaccga ggaaggactc    2700
cgtgttaaaa aaggtggcac taagataaaa gagacaagaa aaagcacaac cagcaatgct    2760
aaaagcaata ctaactccaa accaaataaa aagttagtcc tactaaaagg gtctataaaa    2820
aacccgggaa caaaaaagga atggattctt gtaggatctg ggataaggc caccaaaaac    2880 ggaagctcca gcaacaactc caatacgcaa atatggataa cccgtctagg aacatctgtt    2940
ggttcattaa aaaccgaagg tgagacagtc cttggaattt cgaataataa ttcccaaggg    3000
gaagttctct ggactactat aaatccaaa ctcgaaaacg aaataactc agataacaat    3060 caaatccaat actcccaaag tacgcatagt ttaacaacca attctcgatc aaatacccaa    3120
caatcagggc gaaatcaaat taaaattaca aacacgcaaa ggaaaacaac aacttcgcca    3180
agccaaaatc taagtcaaaa tcctgatctc aaccaaattg atgtaagact tggtctacta    3240
gtacaagaca aaaaacttca cctttggtgg attgctaatg atagctctga tgagcctgag    3300
catataacaa ttgatttcgc tgaagggaca aaattaatt atgatgattt aaattatgtc    3360
ggagggcttt taaaaaatac tacaaataat aacaatatgc aaacccaaga cgatgaaggt    3420
gatggatatc ttgccctaaa aggattaggt atctatgaat ttcctgatga tgaaagtatt    3480
gatcaacccg ctactgttga aaaggcagag agattatata acactttat ggggctattt    3540 agggaataa                                                           3549
```

<210> SEQ ID NO 7
<211> LENGTH: 1053
<212> TYPE: DNA
<213> ORGANISM: Artificial Sequence
<220> FEATURE:
<223> OTHER INFORMATION: mutated mhp389 gene

<400> SEQUENCE: 7

```
atggacaaat tttcacgaac tgttctcggt gatattcacc catcggaatt aggtgttgtt     60
gactgtcatg atcatttaat taaaaattat ggaccaaaag ctcacgaaca tccggatttt    120
gtaatgttat caaatgaggc tgcaattgct gaatcacttg aatatgcttc ccggggtgga    180 aaacaatag tgacaatgga ccccccaaat gttggtcggg atgtctatcg aatgttaaag    240
attgccaaag ctcttgaagg aaaagtgcat attattatgg caactggatt tcataaagcg    300
gctttctatg ataaaggcgc atcatggctt gcgcttgcac caacagatga aattgtaaaa    360
atggttgttg ctgaaattac acagggaatg gatgaatata attattcagg tcctgtggtt    420
agacgttcaa aagccaaagc aggaattatc aaagccggaa ctggatatgg agcaattgat    480
cgacttgaat taaatcact tgaggttgca gcaagagcct caattgaaac cggggcaccg    540
attttggttc atacccaatt aggaacaatg gcctatgaag cggcaaaata tttaattgat    600
tttggtgcaa atccacggaa aattcagatc tcacatctta ataaaaaccc tgataaatat    660
tattatgcaa aaataattaa agaacttggg gtatctttat gttttgatgg tcctgatcgg    720
gttaagtatt ttcctgatac aactcttgct gaaaatatta aatatcttgt cgatttagga    780
```

-continued

```
ctagaaaaac atattacctt atcacttgat gccggtcgtg tttatatca gcgaaattat    840 ggaaaactta aaggtaaatg gacttttgga ctaacctatt tattcgatcg gtttattccg    900
cttttagaac aagttggaat tagcaaggaa acaattaata atattcttgt taataatcca    960
gctgaaattc ttgcctttga tcagccaaga aaatttgatc catcaattct tccagattat   1020
attattgaat taaaaaaatc ctttaaaatc tag                                 1053
```

<210> SEQ ID NO 8
<211> LENGTH: 374
<212> TYPE: PRT
<213> ORGANISM: Mycoplasma hyopneumoniae

<400> SEQUENCE: 8

| | | | | | | | | | | | | | | |
|---|---|---|---|---|---|---|---|---|---|---|---|---|---|---|
| Met | Asp | Lys | Phe | Arg | Tyr | Val | Lys | Pro | Gly | Gln | Ile | Met | Ala | Lys | Asp |
| 1 | | | | 5 | | | | | 10 | | | | | 15 | |
| Glu | Glu | Met | Ile | Arg | Phe | Leu | Asp | Ile | Asp | Gly | Asn | Leu | Leu | Ser | Ser |
| | | | 20 | | | | | 25 | | | | | 30 | | |
| Thr | Val | Phe | Gly | Pro | Ile | Asp | Glu | Thr | Asn | Asp | Ile | Arg | Leu | Ser | Lys |
| | | 35 | | | | | 40 | | | | | 45 | | | |
| Gln | Glu | Ile | Lys | Lys | Ala | Tyr | Glu | Phe | Met | Val | Leu | Ser | Arg | Gln | Gln |
| 50 | | | | | 55 | | | | | 60 | | | | | |
| Asp | Thr | Tyr | Met | Thr | Gln | Leu | Gln | Arg | Gln | Gly | Arg | Met | Leu | Thr | Phe |
| 65 | | | | 70 | | | | | 75 | | | | | 80 | |
| Ala | Pro | Asn | Phe | Gly | Glu | Glu | Ala | Leu | Gln | Val | Ala | Ser | Gly | Met | Ala |
| | | | | 85 | | | | | 90 | | | | | 95 | |
| Leu | Thr | Lys | Asp | Asp | Trp | Phe | Val | Pro | Ala | Phe | Arg | Ser | Asn | Ala | Thr |
| | | | 100 | | | | | 105 | | | | | 110 | | |
| Met | Leu | Tyr | Leu | Gly | Val | Pro | Met | Ile | Leu | Gln | Met | Gln | Tyr | Trp | Asn |
| | | 115 | | | | | 120 | | | | | 125 | | | |
| Gly | Ser | Glu | Lys | Gly | Asn | Val | Ile | Pro | Glu | Asn | Val | Asn | Val | Leu | Pro |
| 130 | | | | | 135 | | | | | 140 | | | | | |
| Ile | Asn | Ile | Pro | Ile | Gly | Thr | Gln | Phe | Ser | His | Ala | Ala | Gly | Ile | Ala |
| 145 | | | | 150 | | | | | 155 | | | | | 160 | |
| Tyr | Ala | Ala | Lys | Leu | Thr | Gly | Lys | Lys | Ile | Val | Ser | Met | Ser | Phe | Ile |
| | | | | 165 | | | | | 170 | | | | | 175 | |
| Gly | Asn | Gly | Gly | Thr | Ala | Glu | Gly | Glu | Phe | Tyr | Glu | Ala | Leu | Asn | Ile |
| | | | 180 | | | | | 185 | | | | | 190 | | |
| Ala | Ser | Ile | Trp | Lys | Trp | Pro | Val | Val | Phe | Cys | Val | Asn | Asn | Asn | Gln |
| | | 195 | | | | | 200 | | | | | 205 | | | |
| Trp | Ala | Ile | Ser | Thr | Pro | Asn | Lys | Tyr | Glu | Asn | Gly | Ala | Ser | Thr | Ile |
| 210 | | | | | 215 | | | | | 220 | | | | | |
| Ala | Ala | Lys | Ala | Met | Ala | Ala | Gly | Ile | Pro | Gly | Ile | Arg | Val | Asp | Gly |
| 225 | | | | 230 | | | | | 235 | | | | | 240 | |
| Asn | Asp | Leu | Leu | Ala | Ser | Tyr | Glu | Val | Ile | Lys | Glu | Ala | Val | Asp | Tyr |
| | | | | 245 | | | | | 250 | | | | | 255 | |
| Ala | Arg | Ser | Gly | Asn | Gly | Pro | Val | Leu | Val | Glu | Phe | Val | Thr | Trp | Arg |
| | | | 260 | | | | | 265 | | | | | 270 | | |
| Gln | Gly | Val | His | Thr | Ser | Ser | Asp | Asn | Pro | Arg | Ile | Tyr | Arg | Thr | Val |
| | | 275 | | | | | 280 | | | | | 285 | | | |
| Glu | Glu | Glu | Arg | Glu | His | Glu | Lys | Trp | Glu | Pro | Met | His | Arg | Ile | Glu |
| 290 | | | | | 295 | | | | | 300 | | | | | |
| Lys | Tyr | Met | Phe | Asp | Arg | Gly | Ile | Leu | Asp | Ser | Ala | Glu | Lys | Gln | Lys |
| 305 | | | | | 310 | | | | | 315 | | | | | 320 |

-continued

```
Ile Trp Asp Glu Ala Leu Ala Ile Val Lys Glu Thr Tyr Glu Lys Ser
                325                 330                 335

Leu Val Gly Leu Glu Ser Thr Ile Asp Glu Ile Phe Asp His Thr Tyr
            340                 345                 350

Lys Val Leu Pro Pro Glu Leu Glu Glu Gln Lys Gln Glu Ala Leu Glu
        355                 360                 365

Phe Phe Lys Gly Val Lys
    370
```

<210> SEQ ID NO 9
<211> LENGTH: 447
<212> TYPE: PRT
<213> ORGANISM: Mycoplasma hyopneumoniae

<400> SEQUENCE: 9

```
Met Lys Trp Asn Lys Phe Leu Gly Leu Gly Leu Val Phe Pro Leu Ser
1               5                   10                  15

Ala Ile Ala Thr Ile Ser Ala Gly Cys Trp Asp Lys Glu Thr Thr Lys
            20                  25                  30

Glu Glu Lys Ser Ala Asp Asn Gln Asn Lys Gln Ile Thr Asp Val Ser
        35                  40                  45

Lys Ile Ser Gly Leu Val Asn Glu Arg Lys Ser Glu Ile Met Ala Ala
    50                  55                  60

Lys Ala Asp Ala Asn Lys His Phe Gly Leu Asn Met Ala Ile Val Thr
65                  70                  75                  80

Ala Asp Gly Thr Val Asn Asp Asn Ser Phe Asn Gln Ser Ser Trp Glu
                85                  90                  95

Ala Ile Gln Gln Leu Gly Ala Leu Thr Gly Gly Glu Ile Thr Ser Val
            100                 105                 110

Asp Ser Ser Thr Ala Glu Leu Glu Gly Lys Tyr Ser Ser Leu Ala Asn
        115                 120                 125

Thr Asn Lys Asn Val Trp Val Leu Ser Gly Phe Gln His Gly Asp Ala
    130                 135                 140

Ile Thr Lys Trp Leu Lys Ile Pro Glu Asn Lys Gln Leu Phe Thr Glu
145                 150                 155                 160

Lys Asn Ile Ile Ile Leu Gly Ile Asp Trp Thr Asp Thr Glu Asn Val
                165                 170                 175

Ile Pro Thr Gly Arg Tyr Ile Asn Leu Thr Tyr Lys Thr Glu Glu Ala
            180                 185                 190

Gly Trp Leu Ala Gly Tyr Ala Asn Ala Ser Phe Leu Ala Lys Lys Phe
        195                 200                 205

Pro Ser Asp Pro Thr Lys Arg Ser Ala Ile Val Ile Gly Gly Gly Ile
    210                 215                 220

Phe Pro Ala Val Thr Asp Phe Ile Ala Gly Tyr Leu Ala Gly Ile Lys
225                 230                 235                 240

Ala Trp Asn Leu Lys Asn Ser Asp Lys Lys Thr Lys Ile Thr Thr Asp
                245                 250                 255

Lys Ile Glu Ile Asn Leu Gly Phe Asp Phe Gln Asn Thr Ser Thr Lys
            260                 265                 270

Glu Arg Leu Glu Gln Ile Ala Ser Lys Asp Lys Pro Ser Thr Leu Leu
        275                 280                 285

Ala Val Ala Gly Pro Leu Thr Glu Ile Phe Ser Asp Ile Ile Ala Asn
    290                 295                 300

Gln Asn Asp Arg Tyr Leu Ile Gly Val Asp Thr Asp Gln Ser Leu Val
305                 310                 315                 320
```

```
Tyr Thr Lys Thr Lys Asn Lys Phe Phe Thr Ser Ile Leu Lys Asn Leu
                325                 330                 335

Gly Tyr Ser Val Phe Ser Val Leu Ser Asp Leu Tyr Thr Lys Lys Ser
            340                 345                 350

Asn Ser Arg Asn Leu Ala Gly Phe Glu Phe Gly Lys Lys Ser Ala Thr
        355                 360                 365

Val Tyr Leu Gly Ile Lys Asp Lys Phe Val Asp Ile Ala Asp Thr Ser
    370                 375                 380

Leu Glu Gly Asn Asp Lys Lys Leu Ala Thr Glu Ala Ile Ser Glu Ala
385                 390                 395                 400

Lys Lys Glu Phe Glu Lys Thr Lys Thr Thr Pro Ala Glu Glu Val
                405                 410                 415

Arg Lys Thr Leu Glu Ile Pro Glu Met Thr Asp Lys Gln Pro Asp Lys
            420                 425                 430

Gln Gln Glu Ser Leu Asp Lys Leu Ile Thr Asp Ile Asn Lys Asn
        435                 440                 445

<210> SEQ ID NO 10
<211> LENGTH: 373
<212> TYPE: PRT
<213> ORGANISM: Mycoplasma hyopneumoniae

<400> SEQUENCE: 10

Ile Ala Ser Arg Ser Asn Thr Thr Ala Lys Val Ala P

```
                245                 250                 255
Lys Phe Leu Pro Gly Ser Gly Lys Val Tyr Ile Thr Gly Val Asp Tyr
            260                 265                 270

Thr Asn Asp Ala Gln Lys Ala Val Leu Asn Asn Lys Leu Ser Ala Thr
        275                 280                 285

Val Glu Gln Asp Thr Asp Leu Leu Gly Arg Leu Ser Leu Ile Ile Ala
    290                 295                 300

Glu Lys Ile Leu Lys Asp Gln Trp Lys Thr Ser Lys Tyr Ser Asp Phe
305                 310                 315                 320

Tyr Ser Gln Phe Pro Gln Leu Asp Lys Asp Lys Asn Pro Asp Asp Gln
            325                 330                 335

Val Glu Gln Gly Tyr Tyr Phe Lys Val Gly Thr Lys Leu Phe Trp Lys
        340                 345                 350

Gly Pro Asp Gly Lys Gly Glu Lys Leu Gln Ala Asp Glu Asn Gly Ile
    355                 360                 365

Leu Gln Lys Val Asn
    370

<210> SEQ ID NO 11
<211> LENGTH: 373
<212> TYPE: PRT
<213> ORGANISM: Mycoplasma hyopneumoniae

<400> SEQUENCE: 11

Ile Ala Ser Arg Ser Asn Thr Thr Ala Lys

```
Ser Ile Ser Ala Leu Glu Ser Ala Gln Ile Pro Leu Gly Gly Gly Asp
                245                 250                 255

Lys Phe Leu Pro Gly Ser Gly Lys Val Tyr Ile Thr Gly Val Asp Tyr
            260                 265                 270

Thr Asn Asp Ala Gln Lys Ala Val Leu Asn Asn Lys Leu Ser Ala Thr
        275                 280                 285

Val Glu Gln Asp Thr Asp Leu Leu Gly Arg Leu Ser Leu Ile Ile Ala
    290                 295                 300

Glu Lys Ile Leu Lys Asp Gln Trp Lys Thr Ser Lys Tyr Ser Asp Phe
305                 310                 315                 320

Tyr Ser Gln Phe Pro Gln Leu Asp Lys Asp Lys Asn Pro Asp Asp Gln
                325                 330                 335

Val Glu Gln Gly Tyr Tyr Phe Lys Val Gly Thr Lys Leu Phe Trp Lys
            340                 345                 350

Gly Pro Asp Gly Lys Gly Glu Lys Leu Gln Ala Asp Glu Asn Gly Ile
        355                 360                 365

Leu Gln Lys Val Asn
    370

<210> SEQ ID NO 12
<211> LENGTH: 691
<212> TYPE: PRT
<213> ORGANISM: Mycoplasma hyopneumoniae

<400> SEQUENCE: 12

Leu Ser Tyr Lys Phe Arg Arg Phe Phe Leu Thr Ser Ala Leu Ser Phe
1               5                   10                  15

Ala Pro Leu Ala Leu Val Ala Ser Cys Val Asn Asn Ser Arg Phe Asp
            20                  25                  30

Ser Asn Glu Asp Asn Lys Leu Val Phe Gly His Thr Phe Ser Ser Ser
        35                  40                  45

Gly Lys Glu Ala Lys Ala Leu Glu Lys Ile Ile Glu Val Trp Asn Lys
    50                  55                  60

Thr Ala Thr Asn Gln Lys Asp Phe Ile Lys Met Glu Ala Gln Tyr Phe
65                  70                  75                  80

Gln Asn Gly Tyr Asn Gly Ser Ala Ala Ser Ile Thr Asn Phe Leu Gln
                85                  90                  95

Thr Lys Asp Arg Ile Lys Leu Pro Asn Ile Val Thr Asn Tyr Pro Ser
            100                 105                 110

Leu Leu Ala Ile Val Asn Lys Tyr Ser Met Thr Phe Pro Leu Val Lys
        115                 120                 125

Asp Phe Ser Ser Asn Gln Glu Pro Gln Asp Glu Asn Glu Lys Ala Ile
    130                 135                 140

Lys Lys Phe Leu Lys Glu Gln Gly Ile Ser Asp Phe Leu Glu Ile Asn
145                 150                 155                 160

Lys Glu Val Pro Phe Leu Asp Thr Lys Gly Val Tyr Thr Leu Pro Phe
                165                 170                 175

Gly Lys Ser Thr Glu Val Leu Thr Ile Asn Lys Val Leu Phe Gly Trp
            180                 185                 190

Met Ile Asn Lys Ala Leu Ala Asp Pro Lys Lys Pro Ala Lys Ile Lys
        195                 200                 205

Glu Glu Asp Lys Pro Tyr Phe Ala Glu Phe Gln Lys Leu Gly Lys Glu
    210                 215                 220

Lys Thr Gly Asp Ile Lys Glu Ile Glu Arg Ile Trp Lys Lys Tyr Val
225                 230                 235                 240
```

```
Ser Asp Asp Gln Gly Leu Ala Gly Tyr Glu Phe Arg Arg Ser Asp Leu
            245                 250                 255
Glu Asn Phe Thr Asp Leu Gln Lys Leu Ser Ser Arg Ile Leu Arg Ser
            260                 265                 270
Phe Pro Glu Ala Leu Ser Gly Gly Ser Thr Asp Ser Ala Lys Ser Val
            275                 280                 285
Leu Gly Ile Asp Asn Gln Ala Thr Leu Val Phe Ala Leu Ala Arg Ser
            290                 295                 300
Val Ser Glu Gly Asn Arg Ser Gln Glu Val Thr Val Leu Asp Arg Gln
305                 310                 315                 320
Lys Asn Leu Ile Asp Tyr Ile Ser Phe Ile Asp Lys Pro Asp Ser Ile
            325                 330                 335
Arg Tyr Lys Asn Leu Glu Lys Ile Phe Asn Leu Leu Ser Gln Gly Ile
            340                 345                 350
Lys Asp Arg Ser Ile Tyr Tyr Thr Ser Ala Gly Glu Tyr Asn Ser Thr
            355                 360                 365
Phe Phe Arg Asn His Gln Gln Val Phe Ser Ile Gly Ser Thr Ser Gly
            370                 375                 380
Tyr Phe His Asn Phe Val Lys Pro Thr Ala Thr Asn Tyr Gln Ile Gly
385                 390                 395                 400
Phe Lys Lys Asn Asp Gly Leu Lys Ser Val Tyr Ser Val Ser Tyr Pro
            405                 410                 415
Lys Phe Ser Ala Ile Val Ser Leu Glu Asp Leu Lys Asp Ile Thr Lys
            420                 425                 430
Asp Leu Glu Ile Thr Ala Thr Asp Gly Ser Ser Lys Leu Lys Ile Asp
            435                 440                 445
Ala Lys Phe Leu Gly Lys Leu Lys Glu Tyr Ala Gln Gln Asn Pro Val
            450                 455                 460
Lys Lys Val Phe Tyr Phe Thr Asp Arg Ser Glu Lys Pro Ser Gly Ile
465                 470                 475                 480
Phe Glu Lys Asp Tyr Ile Val Leu Gly Lys Tyr Lys Asn Asp Lys Asn
            485                 490                 495
Glu Glu Phe Asn Gly Leu Val Ile Pro Thr Tyr Thr Glu Leu Tyr Lys
            500                 505                 510
Asn Ser Gly Ser Asn Ala Leu Asn Asp Asp Glu Leu Ala Leu Glu Ala
            515                 520                 525
Pro Pro His Lys Phe Asp Ala Asn Ser Lys Ile Thr Pro Ile Val Ala
            530                 535                 540
Gln Gly Pro Asp Leu Ile Phe Ile His Ser Thr Glu Lys Glu Asp Lys
545                 550                 555                 560
Ala Ala Lys Ala Phe Val Lys Trp Leu Leu Thr Glu Lys Ile Val Phe
            565                 570                 575
Glu Glu Asn Ser Gln Glu Lys Met Thr Pro Leu Glu Tyr Phe Ala Arg
            580                 585                 590
Ala Thr Ser Tyr Leu Leu Pro Ile Lys Ser Thr Leu Asp Lys Thr His
            595                 600                 605
Phe Ser Pro Lys Asn Arg Ser Gln Lys Phe Ile Leu Asp Gln Phe Ser
            610                 615                 620
Lys Phe Leu Asn Ala Asp Ser Lys Gly Lys Tyr Ser Leu Val Tyr Asp
625                 630                 635                 640
Asn Ala Asp Ala Asn Ala Ser Ser Phe Arg Glu Ser Leu Asp Ser Ser
            645                 650                 655
```

```
Val Ala Gln Met Gln Ser Leu Lys Ala Ser Asp Gly Lys Leu Arg Ser
            660                 665                 670

Phe Lys Glu Phe Leu Glu Lys Leu Glu Gly Asn Leu Gly Pro Ala Phe
        675                 680                 685

Lys Ser Lys
    690

<210> SEQ ID NO 13
<211> LENGTH: 1182
<212> TYPE: PRT
<213> ORGANISM: Mycoplasma hyopneumoniae

<400> SEQUENCE: 13

Ile Gly Leu Thr Ile Phe Glu Lys Ser Phe Ser Ser Gln Val Ser Gly
1               5                   10                  15

Gly Val Asp Lys Asn Lys Val Val Asp Leu Lys Ser Asp Ser Asp Gln
            20                  25                  30

Ile Phe Ser Glu Glu Asp Phe Ile Arg Ala Val Glu Asn Leu Lys Leu
        35                  40                  45

Phe Asp Lys Tyr Lys His Leu Thr Ala Arg Met Ala Leu Gly Leu Ala
    50                  55                  60

Arg Glu Ala Ala Asn Ala Phe Asn Phe Leu Asp Thr Tyr Asp Tyr Thr
65                  70                  75                  80

Pro Ile Thr Lys His Ser Phe Lys Ile Ser Leu Asp Ile Ser Asp Ala
                85                  90                  95

Phe Ala Ala Asn Lys Glu Val Lys Ala Val Val Ser Ala Tyr Ser
            100                 105                 110

Gln Lys Tyr Gln Val Thr Tyr Ser Arg Leu Thr Ser Leu Lys Gly Trp
        115                 120                 125

Lys Glu Glu Asp Asp Phe Gly Asp Asp Ile Ile Asp Tyr Gln Ile Asn
    130                 135                 140

Gln Glu Leu Ser Gly Leu Ser Leu Ser Ser Leu Ala Pro Glu Ser Ala
145                 150                 155                 160

His Leu Leu Ala Ser Glu Met Ala Phe Arg Leu Asp Asn Asp Phe Gln
                165                 170                 175

Val Ala Tyr Lys Lys Thr Gly Ser Arg Ala Glu Ala Phe Arg Gln Ala
            180                 185                 190

Leu Ile Lys Asn Tyr Leu Gly Tyr Asn Leu Val Asn Arg Gln Gly Leu
        195                 200                 205

Pro Thr Met Leu Gln Lys Gly Tyr Val Leu Ala Pro Lys Thr Ile Glu
    210                 215                 220

Asn Lys Asn Ala Ser Glu Glu Lys Leu Val Asn Ile Asn Glu Asn Asp
225                 230                 235                 240

Arg Ala Arg Val Asn Lys Leu Gln Lys Val Glu Asn Leu Ala Phe Lys
                245                 250                 255

Asn Leu Ser Asp Pro Asn Gly Thr Leu Ser Ile Thr Phe Glu Leu Trp
            260                 265                 270

Asp Pro Asn Gly Lys Leu Val Ser Glu Tyr Asp Phe Lys Ile Lys Gly
        275                 280                 285

Ile Lys Lys Leu Asp Phe Asp Leu Lys Lys Gln Glu Glu Lys Val Leu
    290                 295                 300

Gln Lys Val Thr Glu Phe Val Glu Ile Lys Pro Tyr Val Gln Leu Gly
305                 310                 315                 320

Leu Ile Arg Asp Asn Leu Ser Leu Ser Glu Ile Ile Tyr Lys Asn Asp
                325                 330                 335
```

```
Asn Asn Pro Glu Tyr Leu Arg Lys Ile Leu Ala Lys Leu Lys Glu His
            340                 345                 350

Asn Asn Asn Lys Arg Val Asp Asn Asn Thr Ser Thr Thr Lys Phe Gln
            355                 360                 365

Glu Glu Asp Leu Lys Asn Glu Pro Asn Ser Asn Gly Ser Glu Gln Asp
            370                 375                 380

Ser Phe Glu Lys Ala Lys Glu Asn Phe Leu Ser Phe Asp Leu Arg
385                 390                 395                 400

Ser Arg Leu Ile Pro Ile Pro Asp Leu Pro Leu Tyr Tyr Leu Lys Val
                405                 410                 415

Asn Ser Ile Asn Phe Asp Arg Asn Ile Glu Glu Asn Glu Lys Glu Lys
                420                 425                 430

Leu Leu Lys Asn Glu Gln Val Val Leu Lys Val Asp Phe Ser Leu Lys
            435                 440                 445

Lys Val Val Ser Asp Ile Arg Ala Pro Tyr Leu Val Ser Ser Gln Val
            450                 455                 460

Arg Ser Asn Tyr Pro Pro Val Leu Lys Ala Ser Leu Ala Lys Ile Gly
465                 470                 475                 480

Lys Gly Ser Asn Ser Lys Val Val Leu Asp Leu Gly Asn Leu Ser
                485                 490                 495

Ser Arg Phe Lys Val Gln Leu Asp Tyr Ser Ala Lys Gln Arg Glu Ile
            500                 505                 510

Ile Asn Thr Leu Leu Lys Glu Asn Pro Glu Arg Glu Lys Glu Leu Gln
            515                 520                 525

Ala Lys Ile Glu Ser Lys Thr Phe Ser Pro Ile Asp Leu Asn Asn Asp
            530                 535                 540

Asp Leu Leu Ala Ile Glu Phe Gln Tyr Glu Asp Asn Pro Glu Gly Asp
545                 550                 555                 560

Trp Ile Thr Leu Gly Arg Met Glu Lys Leu Val Lys Glu Val Ile Gln
                565                 570                 575

Tyr Lys Lys Glu Gly Lys Thr Phe Leu Asp Asp Glu Val Ala Lys Thr
            580                 585                 590

Leu Tyr Tyr Leu Asp Phe His His Leu Pro Gln Ser Lys Lys Asp Leu
            595                 600                 605

Glu Glu Tyr Lys Glu Lys His Lys Asn Lys Phe Ile Ser Glu Ile Lys
            610                 615                 620

Pro Ala Thr Pro Ala Ser Gln Ala Lys Thr Ser Gln Ala Lys Asn Glu
625                 630                 635                 640

Lys Glu Val Lys Pro Glu Ser Ala Gln Ala Glu Ala Ser Ser Ser Asn
                645                 650                 655

Ser Asn Asp Ser Ser Ser Lys Thr Thr Ser Ser Ser Ser Met Ala Gly
            660                 665                 670

Thr Thr Gln Asn Lys Ser Thr Glu Thr Pro Asn Ser Ser Ser Asn Ser
            675                 680                 685

Thr Pro Thr Ser Ser Ala Thr Thr Ser Ala Thr Thr Ser Thr Thr Ser
            690                 695                 700

Ser Asn Ser Ser Ser Thr Thr Ser Ser Thr Thr Thr Thr Ser Thr
705                 710                 715                 720

Gln Ala Ala Thr Thr Ser Ala Ser Ser Ala Lys Val Lys Thr Thr Lys
                725                 730                 735

Phe Gln Glu Gln Val Lys Glu Gln Glu Gln Lys Gln Glu Lys Ala Lys
            740                 745                 750
```

```
Glu Thr Asn Gln Leu Leu Asp Thr Lys Arg Asn Lys Glu Asp Ser Gly
            755                 760                 765
Leu Gly Leu Ile Leu Trp Asp Phe Leu Val Asn Ser Lys Tyr Lys Thr
        770                 775                 780
Leu Pro Gly Thr Thr Trp Asp Phe His Val Glu Pro Asp Asn Phe Asn
785                 790                 795                 800
Asp Arg Leu Lys Ile Thr Ala Ile Leu Lys Glu Asn Thr Ser Gln Ala
            805                 810                 815
Lys Ser Asn Pro Asp Ser Lys Asn Leu Thr Ser Leu Ser Arg Asn Leu
            820                 825                 830
Ile Ile Lys Gly Val Met Ala Asn Lys Tyr Ile Asp Tyr Leu Val Gln
            835                 840                 845
Glu Asp Pro Val Leu Leu Val Asp Tyr Thr Arg Arg Asn Gln Ile Lys
            850                 855                 860
Thr Glu Arg Glu Gly Gln Leu Ile Trp Ser Gln Leu Ala Ser Pro Gln
865                 870                 875                 880
Met Ala Ser Pro Glu Ser Ser Pro Glu Lys Ala Lys Leu Glu Ile Thr
                    885                 890                 895
Glu Glu Gly Leu Arg Val Lys Lys Gly Thr Lys Ile Lys Glu Thr
                900                 905                 910
Arg Lys Ser Thr Thr Ser Asn Ala Lys Ser Asn Thr Asn Ser Lys Pro
            915                 920                 925
Asn Lys Lys Leu Val Leu Leu Lys Gly Ser Ile Lys Asn Pro Gly Thr
            930                 935                 940
Lys Lys Glu Trp Ile Leu Val Gly Ser Gly Asn Lys Ala Thr Lys Asn
945                 950                 955                 960
Gly Ser Ser Ser Asn Asn Ser Asn Thr Gln Ile Trp Ile Thr Arg Leu
                965                 970                 975
Gly Thr Ser Val Gly Ser Leu Lys Thr Glu Gly Glu Thr Val Leu Gly
                980                 985                 990
Ile Ser Asn Asn Asn Ser Gln Gly Glu Val Leu Trp Thr Thr Ile Lys
            995                 1000                1005
Ser Lys Leu Glu Asn Glu Asn Asn Ser Asp Asn Asn Gln Ile Gln
    1010                1015                1020
Tyr Ser Pro Ser Thr His Ser Leu Thr Thr Asn Ser Arg Ser Asn
    1025                1030                1035
Thr Gln Gln Ser Gly Arg Asn Gln Ile Lys Ile Thr Asn Thr Gln
    1040                1045                1050
Arg Lys Thr Thr Thr Ser Pro Ser Gln Asn Leu Ser Gln Asn Pro
    1055                1060                1065
Asp Leu Asn Gln Ile Asp Val Arg Leu Gly Leu Leu Val Gln Asp
    1070                1075                1080
Lys Lys Leu His Leu Trp Trp Ile Ala Asn Asp Ser Ser Asp Glu
    1085                1090                1095
Pro Glu His Ile Thr Ile Asp Phe Ala Glu Gly Thr Lys Phe Asn
    1100                1105                1110
Tyr Asp Asp Leu Asn Tyr Val Gly Gly Leu Leu Lys Asn Thr Thr
    1115                1120                1125
Asn Asn Asn Asn Met Gln Thr Gln Asp Asp Glu Gly Asp Gly Tyr
    1130                1135                1140
Leu Ala Leu Lys Gly Leu Gly Ile Tyr Glu Phe Pro Asp Asp Glu
    1145                1150                1155
Ser Ile Asp Gln Pro Ala Thr Val Glu Lys Ala Glu Arg Leu Tyr
```

```
                1160                1165                1170
Lys His Phe Met Gly Leu Phe Arg Glu
    1175                1180

<210> SEQ ID NO 14
<211> LENGTH: 350
<212> TYPE: PRT
<213> ORGANISM: Mycoplasma hyopneumoniae

<400> SEQUENCE: 14

Met Asp Lys Phe Ser Arg Thr Val Leu Gly Asp Ile His Pro Ser Glu
1               5                   10                  15

Leu Gly Val Val Asp Cys His Asp Leu Ile Lys Asn Tyr Gly Pro
            20                  25                  30

Lys Ala His Glu His Pro Asp Phe Val Met Leu Ser Asn Glu Ala Ala
            35                  40                  45

Ile Ala Glu Ser Leu Glu Tyr Ala Ser Arg Gly Gly Lys Thr Ile Val
        50                  55                  60

Thr Met Asp Pro Pro Asn Val Gly Arg Asp Val Tyr Arg Met Leu Lys
65                  70                  75                  80

Ile Ala Lys Ala Leu Glu Gly Lys Val His Ile Ile Met Ala Thr Gly
                85                  90                  95

Phe His Lys Ala Ala Phe Tyr Asp Lys Gly Ala Ser Trp Leu Ala Leu
            100                 105                 110

Ala Pro Thr Asp Glu Ile Val Lys Met Val Val Ala Glu Ile Thr Gln
            115                 120                 125

Gly Met Asp Glu Tyr Asn Tyr Ser Gly Pro Val Val Arg Arg Ser Lys
130                 135                 140

Ala Lys Ala Gly Ile Ile Lys Ala Gly Thr Gly Tyr Gly Ala Ile Asp
145                 150                 155                 160

Arg Leu Glu Leu Lys Ser Leu Glu Val Ala Ala Arg Ala Ser Ile Glu
                165                 170                 175

Thr Gly Ala Pro Ile Leu Val His Thr Gln Leu Gly Thr Met Ala Tyr
            180                 185                 190

Glu Ala Ala Lys Tyr Leu Ile Asp Phe Gly Ala Asn Pro Arg Lys Ile
            195                 200                 205

Gln Ile Ser His Leu Asn Lys Asn Pro Asp Lys Tyr Tyr Tyr Ala Lys
        210                 215                 220

Ile Ile Lys Glu Leu Gly Val Ser Leu Cys Phe Asp Gly Pro Asp Arg
225                 230                 235                 240

Val Lys Tyr Phe Pro Asp Thr Thr Leu Ala Glu Asn Ile Lys Tyr Leu
                245                 250                 255

Val Asp Leu Gly Leu Glu Lys His Ile Thr Leu Ser Leu Asp Ala Gly
            260                 265                 270

Arg Val Leu Tyr Gln Arg Asn Tyr Gly Lys Leu Lys Gly Lys Trp Thr
            275                 280                 285

Phe Gly Leu Thr Tyr Leu Phe Asp Arg Phe Ile Pro Leu Leu Glu Gln
        290                 295                 300

Val Gly Ile Ser Lys Glu Thr Ile Asn Asn Ile Leu Val Asn Asn Pro
305                 310                 315                 320

Ala Glu Ile Leu Ala Phe Asp Gln Pro Arg Lys Phe Asp Pro Ser Ile
                325                 330                 335

Leu Pro Asp Tyr Ile Ile Glu Leu Lys Lys Ser Phe Lys Ile
            340                 345                 350
```

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
gatataggat ccatggacaa atttcgctat gtaaagcctg                     40

<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
caatatgtcg acttatttta ctcctttaaa aaattcaagc gcttc               45

<210> SEQ ID NO 17
<211> LENGTH: 51
<212> TYPE: DNA
<213> ORGANISM: Artificial Sequence
<220> FEATURE:
<223> OTHER INFORMATION: primer

<400> SEQUENCE: 17
gatataggat ccatgaatgg aataaatttc ttggcttagg cttagttttt c        51

<210> SEQ ID NO 18
<211> LENGTH: 50
<212> TYPE: DNA
<213> ORGANISM: Artificial Sequence
<220> FEATURE:
<223> OTHER INFORMATION: primer

<400> SEQUENCE: 18
caatatgtcg acttaatttt tattaatatc ggtaattagt ttgtctaagc          50

<210> SEQ ID NO 19
<211> LENGTH: 41
<212> TYPE: DNA
<213> ORGANISM: Artificial Sequence
<220> FEATURE:
<223> OTHER INFORMATION: primer

<400> SEQUENCE: 19
gatataggat ccatgacata ccaagaatat cttcaagcaa g                   41

<210> SEQ ID NO 20
<211> LENGTH: 42
<212> TYPE: DNA
<213> ORGANISM: Artificial Sequence
<220> FEATURE:
<223> OTHER INFORMATION: primer

<400> SEQUENCE: 20
caatatgtcg acctatttac cttcttcaac ttgtagagcg ct                  42

<210> SEQ ID NO 21
<211> LENGTH: 38
<212> TYPE: DNA
<213> ORGANISM: Artificial Sequence
<220> FEATURE:
<223> OTHER INFORMATION: primer -continued

<400> SEQUENCE: 21
gatataggat ccatagcttc aaggtcgaat acaactgc                                38

<210> SEQ ID NO 22
<211> LENGTH: 42
<212> TYPE: DNA
<213> ORGANISM: Artificial Sequence
<220> FEATURE:
<223> OTHER INFORMATION: primer

<400> SEQUENCE: 22
caatatgtcg acttaattta ccttttggag tatcccattt tc                           42

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
gatataggat ccttatccta taaatttagg cgttttttcc                              40

<210> SEQ ID NO 24
<211> LENGTH: 41
<212> TYPE: DNA
<213> ORGANISM: Artificial Sequence
<220> FEATURE:
<223> OTHER INFORMATION: primer

<400> SEQUENCE: 24
caatatgtcg acttattttg atttaaaagc aggacctaaa t                            41

<210> SEQ ID NO 25
<211> LENGTH: 44
<212> TYPE: DNA
<213> ORGANISM: Artificial Sequence
<220> FEATURE:
<223> OTHER INFORMATION: primer

<400> SEQUENCE: 25
gatataggat ccattggact aacaattttt gagaaatcat ttag                         44

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
caatatgtcg acttattcct aaatagcccc ataaagtg                                38

<210> SEQ ID NO 27
<211> LENGTH: 38
<212> TYPE: DNA
<213> ORGANISM: Artificial Sequence
<220> FEATURE:
<223> OTHER INFORMATION: primer

<400> SEQUENCE: 27
gatataggat ccatggacaa attttcacga actgttct                                38

<210> SEQ ID NO 28

```
<211> LENGTH: 51
<212> TYPE: DNA
<213> ORGANISM: Artificial Sequence
<220> FEATURE:
<223> OTHER INFORMATION: primer

<400> SEQUENCE: 28
caatatgtcg acctagattt taaaggattt ttttaattca ataatataat c          51

<210> SEQ ID NO 29
<211> LENGTH: 40
<212> TYPE: DNA
<213> ORGANISM: Artificial Sequence
<220> FEATURE:
<223> OTHER INFORMATION: primer

<400> SEQUENCE: 29
gatataggat ccatggacaa atttcgctat gtaaagcctg                        40

<210> SEQ ID NO 30
<211> LENGTH: 36
<212> TYPE: DNA
<213> ORGANISM: Artificial Sequence
<220> FEATURE:
<223> OTHER INFORMATION: primer

<400> SEQUENCE: 30
gctaacaaaa gatgactggt tgtcccagc ttttcg                             36

<210> SEQ ID NO 31
<211> LENGTH: 36
<212> TYPE: DNA
<213> ORGANISM: Artificial Sequence
<220> FEATURE:
<223> OTHER INFORMATION: primer

<400> SEQUENCE: 31
cgaaaagctg ggacaaacca gtcatctttt gttagc                            36

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
cttgcaaatg caatattgga atggtagcga aaaagg                            36

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33 ccttttttcgc taccattcca atattgcatt tgcaag                           36

<210> SEQ ID NO 34
<211> LENGTH: 58
<212> TYPE: DNA
<213> ORGANISM: Artificial Sequence
<220> FEATURE:
<223> OTHER INFORMATION: primer

<400> SEQUENCE: 34
```

-continued cgaggcgcta aatattgcaa gtatttggaa atggccagtt gttttttgcg taaataac    58

<210> SEQ ID NO 35
<211> LENGTH: 58
<212> TYPE: DNA
<213> ORGANISM: Artificial Sequence
<220> FEATURE:
<223> OTHER INFORMATION: primer

<400> SEQUENCE: 35
gttatttacg caaaaaacaa ctggccattt ccaaatactt gcaatattta gcgcctcg    58

<210> SEQ ID NO 36
<211> LENGTH: 52
<212> TYPE: DNA
<213> ORGANISM: Artificial Sequence
<220> FEATURE:
<223> OTHER INFORMATION: primer

<400> SEQUENCE: 36 gtttttttgcg taaataacaa tcaatgggca atttcaaccc caaataaata tg    52

<210> SEQ ID NO 37
<211> LENGTH: 52
<212> TYPE: DNA
<213> ORGANISM: Artificial Sequence
<220> FEATURE:
<223> OTHER INFORMATION: primer

<400> SEQUENCE: 37
catatttatt tggggttgaa attgcccatt gattgttatt tacgcaaaaa ac    52

<210> SEQ ID NO 38
<211> LENGTH: 36
<212> TYPE: DNA
<213> ORGANISM: Artificial Sequence
<220> FEATURE:
<223> OTHER INFORMATION: primer

<400> SEQUENCE: 38
gttgagtttg taacttggcg tcaaggtgtt catacc    36

<210> SEQ ID NO 39
<211> LENGTH: 36
<212> TYPE: DNA
<213> ORGANISM: Artificial Sequence
<220> FEATURE:
<223> OTHER INFORMATION: primer

<400> SEQUENCE: 39
ggtatgaaca ccttgacgcc aagttacaaa ctcaac    36

<210> SEQ ID NO 40
<211> LENGTH: 32
<212> TYPE: DNA
<213> ORGANISM: Artificial Sequence
<220> FEATURE:
<223> OTHER INFORMATION: primer

<400> SEQUENCE: 40
gagaacacga aaaatgggaa ccaatgcacc gg    32

<210> SEQ ID NO 41
<211> LENGTH: 32
<212> TYPE: DNA

```
<213> ORGANISM: Artificial Sequence
<220> FEATURE:
<223> OTHER INFORMATION: primer

<400> SEQUENCE: 41
ccggtgcatt ggttcccatt tttcgtgttc tc                              32

<210> SEQ ID NO 42
<211> LENGTH: 39
<212> TYPE: DNA
<213> ORGANISM: Artificial Sequence
<220> FEATURE:
<223> OTHER INFORMATION: primer

<400> SEQUENCE: 42
ccgaaaaaca aaaatttgg gatgaagcgc ttgcgattg                         39

<210> SEQ ID NO 43
<211> LENGTH: 39
<212> TYPE: DNA
<213> ORGANISM: Artificial Sequence
<220> FEATURE:
<223> OTHER INFORMATION: primer

<400> SEQUENCE: 43
caatcgcaag cgcttcatcc caaattttt gttttcgg                          39

<210> SEQ ID NO 44
<211> LENGTH: 45
<212> TYPE: DNA
<213> ORGANISM: Artificial Sequence
<220> FEATURE:
<223> OTHER INFORMATION: primer

<400> SEQUENCE: 44
caatatgtcg acttatttta ctcctttaaa aaattcaagc gcttc                 45

<210> SEQ ID NO 45
<211> LENGTH: 52
<212> TYPE: DNA
<213> ORGANISM: Artificial Sequence
<220> FEATURE:
<223> OTHER INFORMATION: primer

<400> SEQUENCE: 45
gatataggat ccatgaaatg gaataaattt cttggcttag gcttagtttt tc         52

<210> SEQ ID NO 46
<211> LENGTH: 40
<212> TYPE: DNA
<213> ORGANISM: Artificial Sequence
<220> FEATURE:
<223> OTHER INFORMATION: primer

<400> SEQUENCE: 46
catttaacca atcaagttgg gaggcaattc aacaacttgg                       40

<210> SEQ ID NO 47
<211> LENGTH: 40
<212> TYPE: DNA
<213> ORGANISM: Artificial Sequence
<220> FEATURE:
<223> OTHER INFORMATION: primer

<400> SEQUENCE: 47
ccaagttgtt gaattgcctc ccaacttgat tggttaaatg                       40
```

<210> SEQ ID NO 48
<211> LENGTH: 45
<212> TYPE: DNA
<213> ORGANISM: Artificial Sequence
<220> FEATURE:
<223> OTHER INFORMATION: primer

<400> SEQUENCE: 48
ctaataccaa caaaaatgtt tgggtacttt ctggttttca acacg                45

<210> SEQ ID NO 49
<211> LENGTH: 45
<212> TYPE: DNA
<213> ORGANISM: Artificial Sequence
<220> FEATURE:
<223> OTHER INFORMATION: primer

<400> SEQUENCE: 49
cgtgttgaaa accagaaagt acccaaacat ttttgttggt attag                45

<210> SEQ ID NO 50
<211> LENGTH: 44
<212> TYPE: DNA
<213> ORGANISM: Artificial Sequence
<220> FEATURE:
<223> OTHER INFORMATION: primer

<400> SEQUENCE: 50
cggtgatgcg atcacaaaat ggttaaaaat ccctgaaaat aagc                 44

<210> SEQ ID NO 51
<211> LENGTH: 44
<212> TYPE: DNA
<213> ORGANISM: Artificial Sequence
<220> FEATURE:
<223> OTHER INFORMATION: primer

<400> SEQUENCE: 51
gcttattttc agggattttt aaccattttg tgatcgcatc accg                 44

<210> SEQ ID NO 52
<211> LENGTH: 45
<212> TYPE: DNA
<213> ORGANISM: Artificial Sequence
<220> FEATURE:
<223> OTHER INFORMATION: primer

<400> SEQUENCE: 52
ttatcatact cggaattgac tggactgata ctgaaaatgt aattc                45

<210> SEQ ID NO 53
<211> LENGTH: 45
<212> TYPE: DNA
<213> ORGANISM: Artificial Sequence
<220> FEATURE:
<223> OTHER INFORMATION: primer

<400> SEQUENCE: 53
gaattacatt ttcagtatca gtccagtcaa ttccgagtat gataa                45

<210> SEQ ID NO 54
<211> LENGTH: 29
<212> TYPE: DNA
<213> ORGANISM: Artificial Sequence
<220> FEATURE:

<223> OTHER INFORMATION: primer

<400> SEQUENCE: 54
gaagaagccg gatggcttgc aggatatgc                               29

<210> SEQ ID NO 55
<211> LENGTH: 29
<212> TYPE: DNA
<213> ORGANISM: Artificial Sequence
<220> FEATURE:
<223> OTHER INFORMATION: primer

<400> SEQUENCE: 55
gcatatcctg caagccatcc ggcttcttc                               29

<210> SEQ ID NO 56
<211> LENGTH: 53
<212> TYPE: DNA
<213> ORGANISM: Artificial Sequence
<220> FEATURE:
<223> OTHER INFORMATION: primer

<400> SEQUENCE: 56
ggttatctag ccggaattaa agcttggaat ctaaaaaatt ctgataaaaa aac     53

<210> SEQ ID NO 57
<211> LENGTH: 53
<212> TYPE: DNA
<213> ORGANISM: Artificial Sequence
<220> FEATURE:
<223> OTHER INFORMATION: primer

<400> SEQUENCE: 57 gttttttat cagaattttt tagattccaa gctttaattc cggctagata acc      53

<210> SEQ ID NO 58
<211> LENGTH: 50
<212> TYPE: DNA
<213> ORGANISM: Artificial Sequence
<220> FEATURE:
<223> OTHER INFORMATION: primer

<400> SEQUENCE: 58
caatatgtcg acttaatttt tattaatatc ggtaattagt ttgtctaagc         50

<210> SEQ ID NO 59
<211> LENGTH: 40
<212> TYPE: DNA
<213> ORGANISM: Artificial Sequence
<220> FEATURE:
<223> OTHER INFORMATION: primer

<400> SEQUENCE: 59
gatataggat ccttatccta taaatttagg cgttttttcc                   40

<210> SEQ ID NO 60
<211> LENGTH: 52
<212> TYPE: DNA
<213> ORGANISM: Artificial Sequence
<220> FEATURE:
<223> OTHER INFORMATION: primer

<400> SEQUENCE: 60
caattaataa agttttgttt ggttggatga ttaataaagc acttgctgat cc     52

<210> SEQ ID NO 61
<211> LENGTH: 52
<212> TYPE: DNA
<213> ORGANISM: Artificial Sequence
<220> FEATURE:
<223> OTHER INFORMATION: primer

<400> SEQUENCE: 61
ggatcagcaa gtgctttatt aatcatccaa ccaaacaaaa ctttattaat tg      52

<210> SEQ ID NO 62
<211> LENGTH: 53
<212> TYPE: DNA
<213> ORGANISM: Artificial Sequence
<220> FEATURE:
<223> OTHER INFORMATION: primer

<400> SEQUENCE: 62
gatattaaag aaattgaaag aatctggaaa aaatatgtct ccgatgatca agg      53

<210> SEQ ID NO 63
<211> LENGTH: 53
<212> TYPE: DNA
<213> ORGANISM: Artificial Sequence
<220> FEATURE:
<223> OTHER INFORMATION: primer

<400> SEQUENCE: 63
ccttgatcat cggagacata ttttttccag attctttcaa tttctttaat atc      53

<210> SEQ ID NO 64
<211> LENGTH: 30
<212> TYPE: DNA
<213> ORGANISM: Artificial Sequence
<220> FEATURE:
<223> OTHER INFORMATION: primer

<400> SEQUENCE: 64 gcccttt cag gaggctccac tgattcggca      30

<210> SEQ ID NO 65
<211> LENGTH: 30
<212> TYPE: DNA
<213> ORGANISM: Artificial Sequence
<220> FEATURE:
<223> OTHER INFORMATION: primer

<400> SEQUENCE: 65
tgccgaatca gtggagcctc ctgaaagggc      30

<210> SEQ ID NO 66
<211> LENGTH: 46
<212> TYPE: DNA
<213> ORGANISM: Artificial Sequence
<220> FEATURE:
<223> OTHER INFORMATION: primer

<400> SEQUENCE: 66
gccgcaaaag cttttgttaa atggcttttg acagaaaaaa tagtct      46

<210> SEQ ID NO 67
<211> LENGTH: 46
<212> TYPE: DNA
<213> ORGANISM: Artificial Sequence
<220> FEATURE:
<223> OTHER INFORMATION: primer

<400> SEQUENCE: 67
agactatttt ttctgtcaaa agccatttaa caaaagcttt tgcggc     46

<210> SEQ ID NO 68
<211> LENGTH: 41
<212> TYPE: DNA
<213> ORGANISM: Artificial Sequence
<220> FEATURE:
<223> OTHER INFORMATION: primer

<400> SEQUENCE: 68
caatatgtcg acttattttg atttaaaagc aggacctaaa t     41

<210> SEQ ID NO 69
<211> LENGTH: 44
<212> TYPE: DNA
<213> ORGANISM: Artificial Sequence
<220> FEATURE:
<223> OTHER INFORMATION: primer

<400> SEQUENCE: 69
gatataggat ccattggact aacaattttt gagaaatcat ttag     44

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
ctaacttctc taaaaggttg gaaagaagaa gatgattttg     40

<210> SEQ ID NO 71
<211> LENGTH: 40
<212> TYPE: DNA
<213> ORGANISM: Artificial Sequence
<220> FEATURE:
<223> OTHER INFORMATION: primer

<400> SEQUENCE: 71
caaaatcatc ttcttctttc caaccttttta gagaagttag     40

<210> SEQ ID NO 72
<211> LENGTH: 47
<212> TYPE: DNA
<213> ORGANISM: Artificial Sequence
<220> FEATURE:
<223> OTHER INFORMATION: primer

<400> SEQUENCE: 72
ctttctatta cttttgaact ctgggaccca aatggtaaat tagtatc     47

<210> SEQ ID NO 73
<211> LENGTH: 47
<212> TYPE: DNA
<213> ORGANISM: Artificial Sequence
<220> FEATURE:
<223> OTHER INFORMATION: primer

<400> SEQUENCE: 73
gatactaatt taccatttgg gtcccagagt tcaaaagtaa tagaaag     47

<210> SEQ ID NO 74
<211> LENGTH: 30

```
<212> TYPE: DNA
<213> ORGANISM: Artificial Sequence
<220> FEATURE:
<223> OTHER INFORMATION: primer

<400> SEQUENCE: 74
ccctgaagga gattggataa ctttagggag                                         30

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
ctccctaaag ttatccaatc tccttcaggg                                         30

<210> SEQ ID NO 76
<211> LENGTH: 34
<212> TYPE: DNA
<213> ORGANISM: Artificial Sequence
<220> FEATURE:
<223> OTHER INFORMATION: primer

<400> SEQUENCE: 76
ctaccaggaa ctacctggga tttccatgtt gaac                                    34

<210> SEQ ID NO 77
<211> LENGTH: 34
<212> TYPE: DNA
<213> ORGANISM: Artificial Sequence
<220> FEATURE:
<223> OTHER INFORMATION: primer

<400> SEQUENCE: 77
gttcaacatg gaaatcccag gtagttcctg gtag                                    34

<210> SEQ ID NO 78
<211> LENGTH: 30
<212> TYPE: DNA
<213> ORGANISM: Artificial Sequence
<220> FEATURE:
<223> OTHER INFORMATION: primer

<400> SEQUENCE: 78
ggacaactaa tttggagcca gttagcttcc                                         30

<210> SEQ ID NO 79
<211> LENGTH: 30
<212> TYPE: DNA
<213> ORGANISM: Artificial Sequence
<220> FEATURE:
<223> OTHER INFORMATION: primer

<400> SEQUENCE: 79
ggaagctaac tggctccaaa ttagttgtcc                                         30

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
```
ggaacaaaaa aggaatggat tcttgtagga tctgg    35

<210> SEQ ID NO 81
<211> LENGTH: 35
<212> TYPE: DNA
<213> ORGANISM: Artificial Sequence
<220> FEATURE:
<223> OTHER INFORMATION: primer

<400> SEQUENCE: 81
ccagatccta caagaatcca ttccttttt gttcc    35

<210> SEQ ID NO 82
<211> LENGTH: 34
<212> TYPE: DNA
<213> ORGANISM: Artificial Sequence
<220> FEATURE:
<223> OTHER INFORMATION: primer

<400> SEQUENCE: 82
ccaatacgca aatatggata acccgtctag gaac    34

<210> SEQ ID NO 83
<211> LENGTH: 34
<212> TYPE: DNA
<213> ORGANISM: Artificial Sequence
<220> FEATURE:
<223> OTHER INFORMATION: primer

<400> SEQUENCE: 83
gttcctagac gggttatcca tatttgcgta ttgg    34

<210> SEQ ID NO 84
<211> LENGTH: 38
<212> TYPE: DNA
<213> ORGANISM: Artificial Sequence
<220> FEATURE:
<223> OTHER INFORMATION: primer

<400> SEQUENCE: 84
ccaaggggaa gttctctgga ctactattaa atccaaac    38

<210> SEQ ID NO 85
<211> LENGTH: 38
<212> TYPE: DNA
<213> ORGANISM: Artificial Sequence
<220> FEATURE:
<223> OTHER INFORMATION: primer

<400> SEQUENCE: 85
gtttggattt aatagtagtc cagagaactt cccttgg    38

<210> SEQ ID NO 86
<211> LENGTH: 37
<212> TYPE: DNA
<213> ORGANISM: Artificial Sequence
<220> FEATURE:
<223> OTHER INFORMATION: primer

<400> SEQUENCE: 86
caaaaaactt cacctttggt ggattgctaa tgatagc    37

<210> SEQ ID NO 87
<211> LENGTH: 37
<212> TYPE: DNA
<213> ORGANISM: Artificial Sequence
<220> FEATURE:
<223> OTHER INFORMATION: primer

<400> SEQUENCE: 87
gctatcatta gcaatccacc aaaggtgaag tttttttg                                37

<210> SEQ ID NO 88
<211> LENGTH: 38
<212> TYPE: DNA
<213> ORGANISM: Artificial Sequence
<220> FEATURE:
<223> OTHER INFORMATION: primer

<400> SEQUENCE: 88
caatatgtcg acttattcct aaatagcccc ataaagtg                                38

<210> SEQ ID NO 89
<211> LENGTH: 38
<212> TYPE: DNA
<213> ORGANISM: Artificial Sequence
<220> FEATURE:
<223> OTHER INFORMATION: primer

<400> SEQUENCE: 89
gatataggat ccatagcttc aaggtcgaat acaactgc                                38

<210> SEQ ID NO 90
<211> LENGTH: 68
<212> TYPE: DNA
<213> ORGANISM: Artificial Sequence
<220> FEATURE:
<223> OTHER INFORMATION: primer

<400> SEQUENCE: 90
aataattgca gaaaaaattc ttaaagatca atggaaaaca agtaaatatt ctgattttta        60
ttcacaat                                                                 68

<210> SEQ ID NO 91
<211> LENGTH: 68
<212> TYPE: DNA
<213> ORGANISM: Artificial Sequence
<220> FEATURE:
<223> OTHER INFORMATION: primer

<400> SEQUENCE: 91
attgtgaata aaaatcagaa tatttacttg ttttccattg atctttaaga atttttctg         60 caattatt                                                                 68

<210> SEQ ID NO 92
<211> LENGTH: 42
<212> TYPE: DNA
<213> ORGANISM: Artificial Sequence
<220> FEATURE:
<223> OTHER INFORMATION: primer

<400> SEQUENCE: 92
caatatgtcg acttaatttta ccttttggag tatcccattt tc                          42

<210> SEQ ID NO 93
<211> LENGTH: 38
<212> TYPE: DNA
<213> ORGANISM: Artificial Sequence
<220> FEATURE:
<223> OTHER INFORMATION: primer

<400> SEQUENCE: 93
gatataggat ccatggacaa attttcacga actgttct                                38

<210> SEQ ID NO 94
<211> LENGTH: 34
<212> TYPE: DNA
<213> ORGANISM: Artificial Sequence
<220> FEATURE:
<223> OTHER INFORMATION: primer

<400> SEQUENCE: 94
caatagtgac aatggacccc ccaaatgttg gtcg                                    34

<210> SEQ ID NO 95
<211> LENGTH: 34
<212> TYPE: DNA
<213> ORGANISM: Artificial Sequence
<220> FEATURE:
<223> OTHER INFORMATION: primer

<400> SEQUENCE: 95
cgaccaacat ttgggggtc cattgtcact attg                                     34

<210> SEQ ID NO 96
<211> LENGTH: 35
<212> TYPE: DNA
<213> ORGANISM: Artificial Sequence
<220> FEATURE:
<223> OTHER INFORMATION: primer

<400> SEQUENCE: 96
gataaaggcg catcatggct tgcgcttgca ccaac                                   35

<210> SEQ ID NO 97
<211> LENGTH: 35
<212> TYPE: DNA
<213> ORGANISM: Artificial Sequence
<220> FEATURE:
<223> OTHER INFORMATION: primer

<400> SEQUENCE: 97
gttggtgcaa gcgcaagcca tgatgcgcct ttatc                                   35

<210> SEQ ID NO 98
<211> LENGTH: 41
<212> TYPE: DNA
<213> ORGANISM: Artificial Sequence
<220> FEATURE:
<223> OTHER INFORMATION: primer

<400> SEQUENCE: 98
ggaaaactta aaggtaaatg gactttggga ctaacctatt t                            41

<210> SEQ ID NO 99
<211> LENGTH: 41
<212> TYPE: DNA
<213> ORGANISM: Artificial Sequence
<220> FEATURE:
<223> OTHER INFORMATION: primer

<400> SEQUENCE: 99
aaataggtta gtccaaaagt ccatttacct ttaagttttc c                            41

<210> SEQ ID NO 100
<211> LENGTH: 51

-continued

```
<212> TYPE: DNA
<213> ORGANISM: Artificial Sequence
<220> FEATURE:
<223> OTHER INFORMATION: primer

<400> SEQUENCE: 100
caatatgtcg acctagattt taaaggattt ttttaattca ataatataat c          51
```

ANTI-*MYCOPLASMA* SPP. SUBUNIT VACCINE

CROSS REFERENCE TO RELATED APPLICATIONS

This application is a Divisional of application Ser. No. 15/383,962, filed on Dec. 19, 2016, which is a Divisional of application Ser. No. 14/765,512, filed on Aug. 3, 2015 (now U.S. Pat. No. 9,561,267, issued Feb. 7, 2017), which was filed as PCT International Application No. PCT/CN2013/071379 on Feb. 5, 2013, all of which are hereby expressly incorporated by reference into the present application.

FIELD OF THE INVENTION

The present disclosure relates to a vaccine against *Mycoplasma* spp.; especially to a subunit vaccine against *Mycoplasma* spp.

BACKGROUND OF THE INVENTION

*Mycoplasma* spp. is currently known the tiniest bacteria capable of self-replication outside host cells. Although swine enzootic pneumonia would not cause swine death, it will reduce feeding efficiency and cause growth retardation, inflammation, and immunosuppression as well as make swine more vulnerable to infection of other pathogens, which therefore become economic damage of the industry.

So far, swine enzootic pneumonia is prevented by three major strategies, including: medicine administration, environment management, and vaccination. Seeing the bad prevention efficiency of antibiotics to *Mycoplasma* hyopneumoniae, medicine administration can only used for treatment purposes and is hard to meet prevention needs. Furthermore, considering that drug abuse may lead to a larger infection causing by drug-resistant bacteria, medicine administration needs cautious plans and exists a lot of limitations.

Environment management forms the basis of prevention of *Mycoplasma* spp. infection. Good piggery sanitation and management would be helpful to reduce occurrence of infection. On the other hand, prevention could be more comprehensive through vaccination.

The conventional vaccines in the field use inactive/dead bacteria as the active ingredient thereof. However, the price of the conventional vaccines is too high because *Mycoplasma* spp. is fastidious bacteria and is difficult to be cultured in the laboratory. In order to reduce the cost of *Mycoplasma* spp. vaccines, scientists continuously try to develop vaccines of different types, such as: (1) attenuated vaccines, (2) vector vaccines, (3) subunit vaccines, and (4) DNA vaccines. Among them, subunit vaccines show the most potential because the advantages of ease in production and high safety.

To date, there are several potential candidate proteins that could be used for *M. hyopneumoniae* vaccines; however, there is no further report verifying the proteins suitable for *M. hyopneumoniae* vaccines.

SUMMARY OF THE INVENTION

In light of the foregoing, one of the objects of the present invention is to provide antigens suitable for being used in *M. hyopneumoniae* vaccines and thereby producing novel *M. hyopneumoniae* vaccines so that the cost of prevention can be reduced.

Another object of the present invention is to provide a combination of antigens that suitable for being used in *M. hyopneumoniae* vaccines and thereby provide subunit vaccines with better performance; therefore, there would be more options for prevention tasks.

In order to achieve the aforesaid objects, the present invention provides a recombination protein for preparing a vaccine for preventing *Mycoplasma* spp. infection, comprising an amino acid sequence of SEQ ID NO: 08, SEQ ID NO: 09, SEQ ID NO: 10, SEQ ID NO: 11, SEQ ID NO: 12, SEQ ID NO: 13, SEQ ID NO: 14, or a combination thereof.

The present invention also provides a vaccine for preventing *Mycoplasma* spp. infection, comprising: an active ingredient, comprising a protein of PdhA, XylF, EutD, Mhp145, P78, P132, Mhp389, or a combination thereof; and a pharmaceutically acceptable adjuvant.

Preferably, said active ingredient is of a concentration of 50 to 3500 µg/mL based on the total volume of said vaccine.

Preferably, said active ingredient comprises at least two proteins selected from a group consisting of PdhA, XylF, EutD, Mhp145, P78, P132, and Mhp389.

Preferably, said active ingredient comprises PdhA and P78.

Preferably, said active ingredient comprises XylF and Mhp145.

Preferably, said pharmaceutically acceptable adjuvant is a complete Freund's adjuvant, an incomplete Freund's adjuvant, an alumina gel, a surfactant, a polyanion adjuvant, a peptide, an oil emulsion, or a combination thereof.

Preferably, said vaccine further comprises a pharmaceutically acceptable additive.

Preferably, said pharmaceutically acceptable additive is a solvent, a stabilizer, a diluent, a preservative, an antibacterial agent, an antifungal agent, an isotonic agent, an absorption delaying agent, or a combination thereof.

The present invention further provides a vaccine for preventing *Mycoplasma* spp. infection, comprising: an active ingredient, comprising an amino acid sequence of SEQ ID NO: 08, SEQ ID NO: 09, SEQ ID NO: 10, SEQ ID NO: 11, SEQ ID NO: 12, SEQ ID NO: 13, SEQ ID NO: 14, or a combination thereof; and a pharmaceutically acceptable adjuvant.

Preferably, said active ingredient is of a concentration of 50 to 3500 µg/mL based on the total volume of said vaccine.

Preferably, said active ingredient comprises at least two amino acid sequences selected from a group consisting of SEQ ID NO: 08, SEQ ID NO: 09, SEQ ID NO: 10, SEQ ID NO: 11, SEQ ID NO: 12, SEQ ID NO: 13, and SEQ ID NO: 14.

Preferably, said active ingredient comprises amino acid sequences of SEQ ID NO: 08 and SEQ ID NO: 12.

Preferably, said active ingredient comprises amino acid sequences of SEQ ID NO: 09 and SEQ ID NO: 11.

Preferably, said pharmaceutically acceptable adjuvant is a complete Freund's adjuvant, an incomplete Freund's adjuvant, an alumina gel, a surfactant, a polyanion adjuvant, a peptide, an oil emulsion, or a combination thereof.

Preferably, said vaccine further comprises a pharmaceutically acceptable additive.

Preferably, said pharmaceutically acceptable additive is a solvent, a stabilizer, a diluent, a preservative, an antibacterial agent, an antifungal agent, an isotonic agent, an absorption delaying agent, or a combination thereof.

The present invention more provides an expression vector for preventing *Mycoplasma* spp. infection, comprising: a plasmid; wherein said plasmid comprises: a nucleotide sequence comprising at least one sequence selected from a group consisting of SEQ ID NO: 01, SEQ ID NO: 02, SEQ ID NO: 03, SEQ ID NO: 04, SEQ ID NO: 05, SEQ ID NO: 06, and SEQ ID NO: 07; and a regulatory element.

Preferably, said regulatory element comprises a promoter and a ribosome binding site.

Preferably, said plasmid is pET-MSY, pET-YjgD, pET-D, or pET-SUMO.

Preferably, said plasmid further comprises a gene encoding a fusion partner.

Preferably, said fusion partner is msyB of E. coli, yjgD of E. coli, protein D of Lambda bacteriophage, or SUMO of S. cerevisiae.

Preferably, said expression vector is used for an E. coli gene expression system.

To sum up, the present invention is related to antigens that are suitable for being used as the active ingredient of a M. hyopneumoniae subunit vaccine and a M. hyopneumoniae subunit vaccine/composition prepared by using the same. The present subunit vaccine not only can be effectively used in prevention task for lowering down the cost thereof, the disclosure of the present invention also shows that a "cocktail" subunit vaccine (i.e. having at least two antigens as active ingredients) using at least two antigens of the present invention has improved induction of immune response.

BRIEF DESCRIPTION OF THE DRAWINGS

The patent or application file contains at least one color drawing. Copies of this patent or patent application publication with color drawing will be provided by the USPTO upon request and payment of the necessary fee.

DESCRIPTION OF REFERENCE SIGNS IN THE FIGURES

Figure 1:
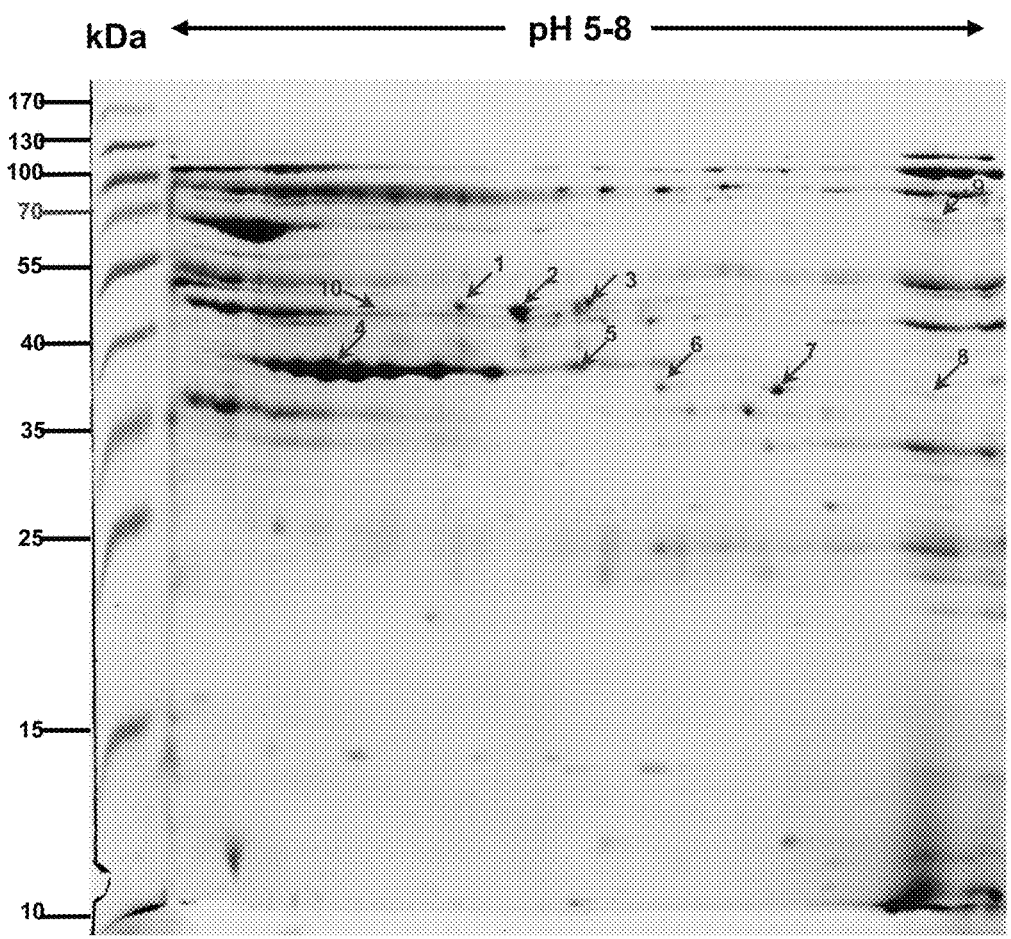
FIG. 1 shows the result of the two-dimensional gel protein electrophoresis conducted in the $1^{st}$ example of the present invention.

1 XylF(xylose-binding lipoprotein)
2 XylF(xylose-binding lipoprotein)
3 XylF(xylose-binding lipoprotein)
4 PdhA(pyruvate dehydrogenase E1-alpha subunit)
5 Mhp145(periplasmic sugar-binding protein)
6 EutD(phosphotransacetylase)
7 EutD(phosphotransacetylase)
8 Mhp389
9 P78(lipoprotein)
10 P132

DETAILED DESCRIPTION OF THE INVENTION

One of the core concepts of the present invention is to survey potential candidate antigens suitable for subunit vaccines by using two-dimensional gel protein electrophoresis along with immunological screening technology and to identify the antigens by mass spectrometer. Then, the performance of the present subunit vaccines were verified by animal model experiments.

Briefly, the progress of the development of the present invention is:

(1) Inducing immune response of experiment pigs by injecting a conventional M. hyopneumoniae vaccine and obtaining serum containing anti-M. hyopneumoniae antibodies. (2) Obtaining total proteins of M. hyopneumoniae for two-dimensional gel protein electrophoresis. (3) Conducting hybridization of the result of the two-dimensional gel protein electrophoresis of step (2) by using the serum of step (1) as $1^{st}$ antibody, and then collecting proteins showing positive (i.e. candidate antigens) from the gel after amplification by a $2^{nd}$ antibody and the following development procedure. (4) Identifying the candidate antigens obtained in step (3). (5) Expressing said candidate antigens in large amounts by using an E. coli gene expression system. (6) Examining the efficacy of the present subunit vaccines in reducing pathological traits in lung by swine challenge experiments and thereby verifying the value of said candidate antigens in being used as active ingredient of a subunit vaccine.

The present vaccine for preventing Mycoplasma spp. infection comprises an active ingredient and a pharmaceutically acceptable adjuvant.

In an embodiment of the present invention, said active ingredient may be PdhA, XylF, EutD, Mhp145, P78, P132, or Mhp389. In an alternative embodiment, as long as the antigenic determinant of any of the aforesaid protein is not interfered, said active ingredient may be a fusion protein of any two of the aforesaid proteins. In another alternative embodiment, said active ingredient comprises at least two of the aforesaid proteins; that is, so called a "cocktail" vaccine of the present invention.

In another embodiment of the present invention, said active ingredient may comprise an amino acid sequence of SEQ ID NO: 08, SEQ ID NO: 09, SEQ ID NO: 10, SEQ ID NO: 11, SEQ ID NO: 12, SEQ ID NO: 13, SEQ ID NO: 14, or a combination thereof. In an alternative embodiment, as long as the antigenic determinant formed by folding of a peptide of said amino acid sequence is not interfered, said active ingredient may be a fusion protein with at least two said sequences. In another alternative embodiment, said active ingredient comprises two or more proteins respectively comprising one of the aforesaid amino acid sequences; that is, so called a "cocktail" vaccine of the present invention.

Said pharmaceutically acceptable adjuvant is used for improving the immune effect of said active ingredient, stabilizing said active ingredient, and/or increasing the safety of vaccines. Said pharmaceutically acceptable adjuvant of the present invention includes, but not limits to: a complete Freund's adjuvant, an incomplete Freund's adjuvant, an alumina gel, a surfactant, a polyanion adjuvant, a peptide, an oil emulsion, or a combination thereof.

The vaccine of the present invention may have one or at least two said active ingredients (i.e. a cocktail vaccine). In an example of the present vaccine, said active ingredient is of a concentration of 50 to 3500 μg/mL based on the total volume of said vaccine. In a preferable embodiment of the present invention, when said vaccine comprises only one said active ingredient, said active ingredient is of a concentration of 50 to 500 μg/mL based on the total volume of said vaccine. In an alternative embodiment of the present invention, the present vaccine comprises at least one said active ingredient; wherein the total concentration of said active ingredient(s) contained in said vaccine is 50 to 1000 μg/mL, 50 to 1500 µg/mL, 50 to 2000 µg/mL, 50 to 2500 µg/mL, 50 to 3000 µg/mL, or 50 to 3500 µg/mL based on the total volume of said vaccine.

Another aspect of the present invention is to provide an expression vector for preventing *Mycoplasma* spp. infection. Specifically, said expression vector may be used for an *E. coli* gene expression system. Nevertheless, without being apart from the spirit of the present invention, those having ordinary skill in the art can modify said vector based on the disclosure of the present invention and make said vector suitable for different gene expression system while still belongs to the scope of the present invention.

Said expression vector comprises a plasmid. Said plasmid comprises: a nucleotide sequence comprising at least one sequence selected from a group consisting of SEQ ID NO: 01, SEQ ID NO: 02, SEQ ID NO: 03, SEQ ID NO: 04, SEQ ID NO: 05, SEQ ID NO: 06, SEQ ID NO: 07, and a combination thereof; and a regulatory element.

Said vector is used in an *E. coli* gene expression system and for producing the antigens of the present invention via *E. coli*. In other words, said nucleotide sequence can be translated into the amino sequence of the present antigen via an *E. coli* gene expression system and then the amino acid sequence can fold into the present antigen.

In an alternative embodiment, as long as the operation of the *E. coli* gene expression system is not hindered and the production of said nucleotide sequence and the folding of the consequent amino acid sequence thereof are not interfered, said plasmid may comprise two or more said nucleotide sequences.

Said regulatory element is referred to an element required for initiating the transcription and translation in the expression system. Said regulatory element shall at least comprise a promoter, and a ribosome binding site. Preferably, said regulatory element may further comprise: an operator, an enhancer sequence, or a combination thereof.

In a preferable embodiment of the present invention, said plasmid further comprises a gene encoding a fusion partner. Said fusion partner includes but not limits to msyB of *E. coli*, yjgD of *E. coli*, protein D of Lambda bacteriophage, or SUMO of *S. cerevisiae*. Said MsyB is rich in acidic amino acid and might be favorable for improving the solubility of the proteins to be produced.

The following examples recite the trials and experiments of the present invention in order to further explain the features and advantages of the present invention. It shall be noted that the following examples are exemplary and shall not be used for limiting the claim scope of the present invention.

Example 1: Screening for Candidate Antigens Suitable for being Used as Active Ingredient of a Subunit Vaccine Preparation of Serum Containing Anti-Swine *Mycoplasm* spp. Antibody According to researches, there are seven *Mycoplasm* spp. can be isolated from swine: *Mycoplasm hyopneumoniae, Mycoplasma hyorhinis, Mycoplasma hyosynoviae, Mycoplasma flocculare, Mycoplasma hyopharyngis, Mycoplasma sualvi, Mycoplasma bovigenitalium* (Gourlay et al., 1978; Blank et al., 1996; Assuncao et al., 2005). Among them, *M. hyopneumoniae* is the major pathogen of swine enzootic pneumonia with an infection rate of 25 to 93%. Therefore, the present invention used *M. hyopneumoniae* (PRIT-5 strain) for immune proteomics studies and as sources of genes encoding antigens. Friis medium (Friis et al., 1975) as used for culturing *M. hyopneumoniae*. According to the experiment design, a proper amount of antibiotic or agar of 1.5% was added to formulating a solid medium.

Three SPF pigs of 4-week old were brought from Agricultural Technology Research Institute and fed with same feed and kept at same environment and growth condition in piggery before experiments.

After the pigs were fed to 32-day, 46-day, and 60-day old, the pigs were administrated 2 mL of Bayovac® MH-PRIT-5 (*M. hyopneumoniae* PRIT-5) vaccine via intramuscular injection. Then, the pigs were continuously fed to 74-day old and blood was collected from a jugular vein thereof. The collected blood was placed in room temperature for 1 hour and stored in 4° C. In the next day, the collected blood was centrifugated at 1,107×g for 30 minutes and the supernatant was removed to a clean tube and stored in −20° C.

Two-Dimensional Gel Protein Electrophoresis of the Total Protein of *Mycoplasm* spp.

ReadyPrep™ protein extraction kit (total protein) (Bio-Rad, CA, USA) was used for extracting the total protein of *Mycoplasm* spp. Afterward, the concentration of the protein collected was determined by using a Bio-Rad RC DC Protein Assay Kit (CA, USA). The detailed protocol can be referred from the product description or can be modified from well-known protocols in the field.

The two-dimensional gel protein electrophoresis was conducted in two steps: isoelectric focusing (IEF) and sodium dodecyl sulfate-polyacrylamide gel electrophoresis (SDS-PAGE). IEF was to separate proteins in the sample in view of isoelectric point thereof. SDS-PAGE was to separate proteins accordance with molecular weight thereof. Please see FIG. 1, which shows the result of the two-dimensional gel protein electrophoresis.

Hybridization

The serum obtained in step (1) was used as $1^{st}$ antibody to hybridize with the result of the two-dimensional gel protein electrophoresis in step (2). After being amplified by $2^{nd}$ antibody and developed by the following development procedure, proteins showing positive were collected. Those proteins were recognized by the anti-*Mycoplasm* spp. antibody and therefore would be suitable as candidate antigens for active ingredient of subunit vaccines.

The hybridization was conducted by Western blotting. Briefly, the 2D gel after electrophoresis was transferred to a PVDF membrane. Then, the membrane was incubated and hybridized sequentially with $1^{st}$ antibody (the serum containing anti-*Mycoplasm* spp. antibody) and $2^{nd}$ antibody (AP-conjugated anti-pig IgG). Afterward, a color reaction was conducted by using NBT/BCIP solution.

Figure 2:
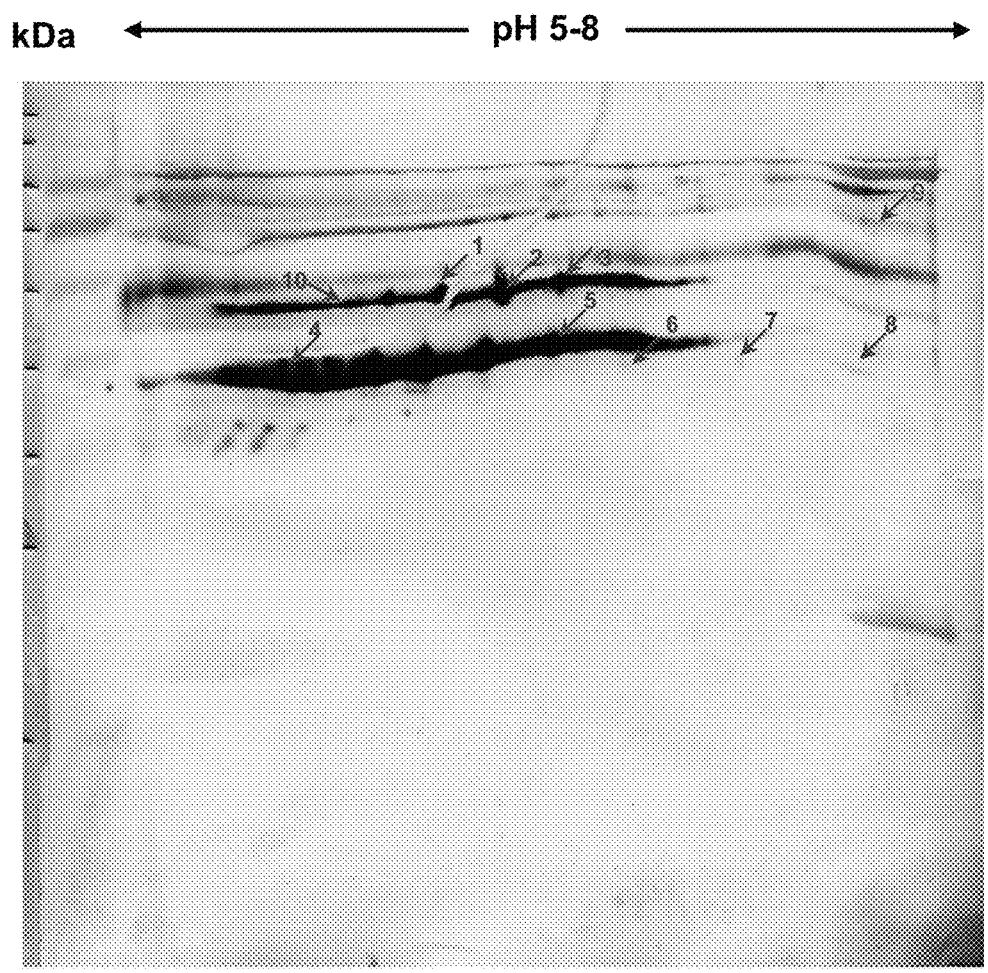
FIG. 2 shows the result of the color reaction of the Western blot conducted in the $1^{st}$ example of the present invention.

The result of the color reaction of Western blotting was shown in FIG. 2; wherein 10 proteins positive to the immuno-hybridization with anti-*Mycoplasm* spp. antibody were marked as candidate antigens for being used as active ingredients of subunit vaccines.

Identification of the Candidate Antigens Obtained

According to the color reaction of the Western blotting, the gel corresponding to the positive location on the membrane was cut by micropeptide and analyzed by mass spectrometry. The obtained data of the mass spectrometry was then matched with amino acid sequence and protein database to identify those proteins.

Please see the following table 1, said 10 proteins positive to the immune-hybridization with anti-*Mycoplasm* spp. antibody were listed.

TABLE 1 the 10 proteins positive to the immune-hybridization with anti-*Mycoplasm* spp. antibody and amino sequence thereof.

| Candidate | Name | SEQ ID NO |
|---|---|---|
| 1 | XylF (xylose-binding lipoprotein) | SEQ ID NO: 09 |
| 2 | XylF (xylose-binding lipoprotein) | SEQ ID NO: 09 |
| 3 | XylF (xylose-binding lipoprotein) | SEQ ID NO: 09 |
| 4 | PdhA (pyruvate dehydrogenase E1-alpha subunit) | SEQ ID NO: 08 |
| 5 | Mhp145 (periplasmic sugar-binding protein) | SEQ ID NO: 11 |
| 6 | EutD (phosphotransacetylase) | SEQ ID NO: 10 |
| 7 | EutD (phosphotransacetylase) | SEQ ID NO: 10 |
| 8 | Mhp389 | SEQ ID NO: 14 |
| 9 | P78 (lipoprotein) | SEQ ID NO: 12 |
| 10 | P132 | SEQ ID NO: 13 |

*XylF and EutD have different charge states in cells and therefore become 3 and 2 positive location on the membrane.

Example 2: Expressing of Said Candidate Antigens in Large Amount by *E. coli* Gene Expression System

*Escherichia coli* JM109 was used as the host cells for cloning and *Escherichia coli* BL21 (DE3) was used as the host cells for protein expression. The *Escherichia coli* cells were cultured in LB medium (Luria-Bertani; Difco, Mich., USA). According to the experiment design, a proper amount of antibiotic or agar of 1.5% was added to formulating a solid medium.

Amplification of the Genes Encoding the Candidate Antigens

After the candidate antigens were identified, the genes encoding those antigens were searched in the NCBI database (National Center for Biotechnology Information). Specific primers targeting the antigen genes were designed accordingly. Then, the antigen genes were amplified by using the specific primers and the chromosome of *M. hyopneumoniae* PRIT-5 as template. The specific primers used were listed in the following table 2.

TABLE 2

Primer set.

| Candidate | Sequences of the primer set |
|---|---|
| PdhA | PdhAF (SEQ ID NO: 15)<br>5'-GATATAGGATCCATGGACAAATTTCGCTATG TAAAGCCT G-3' PdhAR (SEQ ID NO: 16)<br>5'-CAATATGTCGACTTATTTTACTCCTTTAAAA AATTCAAGCGCTTC-3' |
| XylF | XylFF (SEQ ID NO: 17)<br>5'-GATATAGGATCCATGAATGGAATAAATTTCT TGGCTTAGGCTTAGTTTTTC-3'<br>XylFR (SEQ ID NO: 18)<br>5'-CAATATGTCGACTTAATTTTTATTAATATCG GTAATTAGTTTGTCTAAGC-3' |
| EutD | EUTDF (SEQ ID NO: 19)<br>5'-GATATAGGATCCATGACATACCAAGAATATC TTCAAGCAA G-3') |

TABLE 2-continued

Primer set.

| Candidate | Sequences of the primer set |
|---|---|
| | EUTDR (SEQ ID NO: 20)<br>5'-CAATATGTCGACCTATTTACCTTCTTCAAC TTGTAGAGCGCT-3') |
| Mhp145 | Mhp145F (SEQ ID NO: 21)<br>5'-GATATAGGATCCATAGCTTCAAGGTCGAA TACAACTGC-3' Mhp145R (SEQ ID NO: 22)<br>5'-CAATATGTCGACTTAATTTACCTTTTGGAG TATCCCATTTTC-3' |
| P78 | P78F (SEQ ID NO: 23)<br>5'-GATATAGGATCCTTATCCTATAAATTTAGG CGTTTTTTCC-3' P78R (SEQ ID NO: 24)<br>5'-CAATATGTCGACTTATTTTGATTTAAAAGCA GGACCTAA AT-3' |
| P132 | PI32F (SEQ ID NO: 25)<br>5'-GATATAGGATCCATTGGACTAACAATTTTTG AGAAATCATTTAG-3'<br>P132R (SEQ ID NO: 26)<br>5'-CAATATGTCGACTTATTCCTAAATAGCCCC ATAAAGTG-3' |
| Mhp389 | Mhp389F (SEQ ID NO: 27)<br>5'-GATATAGGATCCATGGACAAATTTTCACGA ACTGTTCT-3' Mhp389R (SEQ ID NO: 28)<br>5'-CAATATGTCGACCTAGATTTTAAAGGATTTTT TTAATTCAATAATATAATC-3' |

Figure 3:
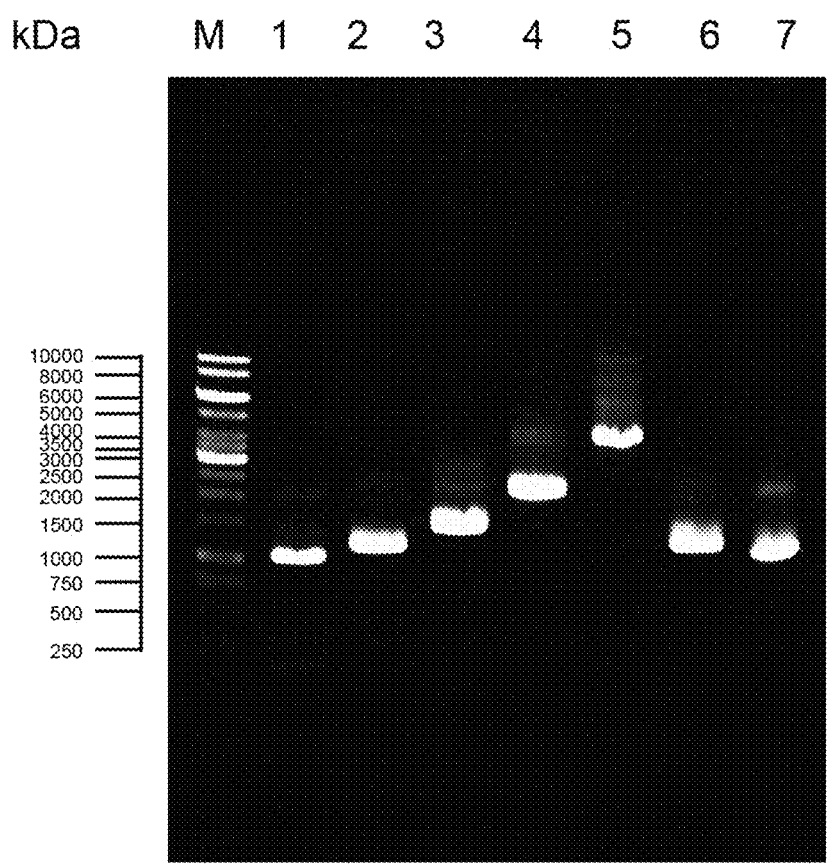
FIG. 3 shows the result of the electrophoresis of the PCR products obtained in the $2^{nd}$ example of the present invention.

Polymerase chain reaction (PCR) was conducted with the primer sets listed in the table 2 above to amplify the genes of the candidate antigens. The amplified genes were then used in the *E. coli* gene expression system. The PCR condition was: 5 minutes in 98° C. (one round); 30 seconds in 94° C., 30 seconds in 55° C., X seconds in 68° C. (35 rounds); 5 minutes in 68° C. (one round). Said X was the elongation time for the DNA polymerase and was set depending on the size of the fragment to be amplified. After the PCR reaction, an electrophoresis was conducted to verify if the PCR products contained the DNA fragments of expected size. Please see FIG. 3, which shows the electrophoresis result of the PCR products; wherein lane 1 was eutD gene; lane 2 was pdhA; lane 3 was xylF; lane 4 was P78 gene; lane 5 was P132 gene; lane 6 was mhp145; lane 7 was mhp389.

Cloning of the PCR Products

The cloning was conducted by using a CloneJET PCR Cloning Kit, and the ligation mixture was transformed into *E. coli* ECOS™ 9-5 (Yeastern, Taipei, Taiwan). The detailed protocol can be referred from the product description or modified from the well-known protocol in the field.

After transformation, the bacteria were cultured on a solid LB medium containing ampicillin (100 μg/mL) until colony thereof formed. Then, colony PCR was conducted to screen strains success in transformation. The PCR condition was: 5 minutes in 95° C. (one round); 30 seconds in 95° C., 30 seconds in 55° C., X seconds in 72° C. (25 rounds); 7 minutes in 72° C. (one round). Said X was the elongation time for the DNA polymerase and was set depending on the size of the fragment to be amplified. The elongation speed of Taq DNA polymerase (Genomics, Taipei, Taiwan) is 1 kb/min; therefore, if Taq DNA polymerase is used for amplifying a 1 kb DNA fragment, said X shall be set as 1 minute.

The plasmids of strains, whose recombinant plasmids were verified having the insert DNA, were then proceeded to DNA sequencing (Total Solution Provider of Systems Biology and Chemoinformatics Ltd.). Plasmids containing eutD, pdhA, xylF, P78 gene, P132 gene, mhp145, and mhp389 were named as pJET-eutD, pJET-pdhA, pJET-xylF, pJET-P78, pJET-P132, pJET-mhp145, pJET-mhp389, respectively.

Point Mutation and Cloning of the Antigen Genes of *M. hyopneumoniae*

Before amplifying the candidate antigens in an *E. coli* gene expression system, the codon usage in different organisms shall be considered. That said, if the gene contains codon that would be encoded ambiguously between the original organism therefrom and *E. coli*, the gene shall be modified by point mutation.

The *M. hyopneumoniae* antigen genes, pdhA, xylF, P78 gene, P132 gene, mhp145, and mhp389, contain TGA codon (eutD does not have the concern in codon usage like others). The TGA codon was translated into tryptophan in *Mycoplasma* spp. but translated as stop codon in *E. coli*. In order to prevent from not being able to produce the entire protein in an *E. coli* gene expression system, primers targeting the TGA site were designed and point mutation replacing TGA with TGG was conducted by using overlapping extension polymerase chain reaction. As a result, the genes to be expressed in the *E. coli* gene expression system can be truthfully translated into the candidate antigen of the present invention. Besides, the cutting sites of BamHI of P78 gene, P132 gene, and mhp389 were undergone silent mutation for the convenience of cloning.

The primers used for point mutation was designed to locate the site of point mutation at the central part of the primer and to have a Tm value of higher than 78° C. The Tm value of the primers for point mutation was calculated by using the formula provided by Invitrogene Co.: Tm=81.5+ 0.41 (% GC)−675/N−% mismatch; wherein % GC is referred as the percentage of GC in view of the total nucleotides contained in the primer concerned; N is referred as the length of the primer concerned; % mismatch is referred as the percentage of the base to be mutated in view of the total nucleotides contained in the primer concerned. The primer sets used for the aforesaid genes were listed in the following Table 3 to Table 8.

TABLE 3

The primer sets for point mutation of pdhA.

| Primer | DNA sequence (5' to 3') |
| --- | --- |
| PdhAF SEQ ID NO: 29 | GATATAGGATCCATGGACAAATTTCGCTATGTAAAG CCTG |
| PdhAM1 SEQ ID NO: 30 | GCTAACAAAAGATGACTGGTTTGTCCCAGCTTTTCG |
| PdhAM2 SEQ ID NO: 31 | CGAAAAGCTGGGACAAACCAGTCATCTTTTGTTAGC |
| PdhAM3 SEQ ID NO: 32 | CTTGCAAATGCAATATTGGAATGGTAGCGAAAAAGG |
| PdhAM4 SEQ ID NO: 33 | CCTTTTTCGCTACCATTCCAATATTGCATTTGCAAG |
| PdhAM5 SEQ ID NO: 34 | CGAGGCGCTAAATATTGCAAGTATTTGGAAATGGCC AGTTGTTTTTGCGTAAATAAC |
| PdhAM6 SEQ ID NO: 35 | GTTATTTACGCAAAAAACAACTGGCCATTTCCAAAT ACTTGCAATATTTAGCGCCTCG |
| PdhAM7 SEQ ID NO: 36 | GTTTTTTGCGTAAATAACAATCAATGGGCAATTTCA ACCCCAAATAAATATG |
| PdhAM8 SEQ ID NO: 37 | CATATTTATTTGGGGTTGAAATTGCCCATTGATTGT TATTTACGCAAAAAAC |
| PdhAM9 SEQ ID NO: 38 | GTTGAGTTTGTAACTTGGCGTCAAGGTGTTCATACC |
| PdhAM10 SEQ ID NO: 39 | GGTATGAACACCTTGACGCCAAGTTACAAACTCAAC |

TABLE 3-continued

The primer sets for point mutation of pdhA.

| Primer | DNA sequence (5' to 3') |
| --- | --- |
| PdhAM11 SEQ ID NO: 40 | GAGAACACGAAAAATGGGAACCAATGCACCGG |
| PdhAM12 SEQ ID NO: 41 | CCGGTGCATTGGTTCCCATTTTTCGTGTTCTC |
| PdhAM13 SEQ ID NO: 42 | CCGAAAAACAAAAAATTTGGGATGAAGCGCTTGCGA TTG |
| PdhAM14 SEQ ID NO: 43 | CAATCGCAAGCGCTTCATCCCAAATTTTTTGTTTTT CGG |
| PdhAR SEQ ID NO: 44 | CAATATGTCGACTTATTTTACTCCTTTAAAAAATTC AAGCGCTTC |

TABLE 4

The primer sets for point mutation of xylF.

| Primer | DNA sequence (5' to 3') |
| --- | --- |
| XylFF SEQ ID NO: 45 | GATATAGGATCCATGAAATGGAATAAATTTCTTGGC TTAGGCTTAGTTTTTC |
| XylFM1 SEQ ID NO: 46 | CATTTAACCAATCAAGTTGGGAGGCAATTCAACAAC TTGG |
| XylFM2 SEQ ID NO: 47 | CCAAGTTGTTGAATTGCCTCCCAACTTGATTGGTTA AATG |
| XylFM3 SEQ ID NO: 48 | CTAATACCAACAAAAATGTTTGGGTACTTTCTGGTT TTCAACACG |
| XylFM4 SEQ ID NO: 49 | CGTGTTGAAAACCAGAAAGTACCCAAACATTTTTGT TGGTATTAG |
| XylFM5 SEQ ID NO: 50 | CGGTGATGCGATCACAAAATGGTTAAAAATCCCTGA AAATAAGC |
| XylFM6 SEQ ID NO: 51 | GCTTATTTTCAGGGATTTTTAACCATTTTGTGATCG CATCACCG |
| XylFM7 SEQ ID NO: 52 | TTATCATACTCGGAATTGACTGGACTGATACTGAAA ATGTAATTC |
| XylFM8 SEQ ID NO: 53 | GAATTACATTTTCAGTATCAGTCCAGTCAATTCCGA GTATGATAA |
| XylFM9 SEQ ID NO: 54 | GAAGAAGCCGGATGGCTTGCAGGATATGC |
| XylFM10 SEQ ID NO: 55 | GCATATCCTGCAAGCCATCCGGCTTCTTC |
| XylFM11 SEQ ID NO: 56 | GGTTATCTAGCCGGAATTAAAGCTTGGAATCTAAAA AATTCTGATAAAAAAAC |
| XylFM12 SEQ ID NO: 57 | GTTTTTTTATCAGAATTTTTTAGATTCCAAGCTTTA ATTCCGGCTAGATAACC |
| XylFR SEQ ID NO: 58 | CAATATGTCGACTTAATTTTTATTAATATCGGTAAT TAGTTTGTCTAAGC |

TABLE 5

The primer sets for point mutation of P78 gene.

| Primer | DNA sequence (5' to 3') |
| --- | --- |
| P78F SEQ ID NO: 59 | GATATAGGATCCTTATCCTATAAATTTAGGCGTTTT TTCC |
| P78M1 SEQ ID NO: 60 | CAATTAATAAAGTTTTGTTTGGTTGGATGATTAATA AAGCACTTGCTGATCC |
| P78M2 SEQ ID NO: 61 | GGATCAGCAAGTGCTTTATTAATCATCCAACCAAAC AAAACTTTATTAATTG |
| P78M3 SEQ ID NO: 62 | GATATTAAAGAAATTGAAAGAATCTGGAAAAAATAT GTCTCCGATGATCAAGG |
| P78M4 SEQ ID NO: 63 | CCTTGATCATCGGAGACATATTTTTTCCAGATTCTT TCAATTTCTTTAATATC |
| P78M5 SEQ ID NO: 64 | GCCCTTTCAGGAGGCTCCACTGATTCGGCA |
| P78M6 SEQ ID NO: 65 | TGCCGAATCAGTGGAGCCTCCTGAAAGGGC |
| P78M7 SEQ ID NO: 66 | GCCGCAAAAGCTTTTGTTAAATGGCTTTTGACAGAA AAAATAGTCT |
| P78M8 SEQ ID NO: 67 | AGACTATTTTTCTGTCAAAAGCCATTTAACAAAAG CTTTTGCGGC |

TABLE 5-continued

The primer sets for point mutation of P78 gene.

| Primer | DNA sequence (5' to 3') |
|---|---|
| P78R<br>SEQ ID NO: 68 | CAATATGTCGACTTATTTTGATTTAAAAGCAGGACC<br>TAAAT |

TABLE 6

The primer sets for point mutation of P132 gene.

| Primer | DNA sequence (5' to 3') |
|---|---|
| P132F<br>SEQ ID NO: 69 | GATATAGGATCCATTGGACTAACAATTTTTGAGAAA<br>TCATTTAG |
| P132M1<br>SEQ ID NO: 70 | CTAACTTCTCTAAAAGGTTGGAAAGAAGAAGATGAT<br>TTTG |
| P132M2<br>SEQ ID NO: 71 | CAAAATCATCTTCTTCTTTCCAACCTTTTAGAGAAG<br>TTAG |
| P132M3<br>SEQ ID NO: 72 | CTTTCTATTACTTTTGAACTCTGGGACCCAAATGGT<br>AAATTAGTATC |
| P132M4<br>SEQ ID NO: 73 | GATACTAATTTACCATTTGGGTCCCAGAGTTCAAAA<br>GTAATAGAAAG |
| P132M5<br>SEQ ID NO: 74 | CCCTGAAGGAGATTGGATAACTTTAGGGAG |
| P132M6<br>SEQ ID NO: 75 | CTCCCTAAAGTTATCCAATCTCCTTCAGGG |
| P132M7<br>SEQ ID NO: 76 | CTACCAGGAACTACCTGGGATTTCCATGTTGAAC |
| P132M8<br>SEQ ID NO: 77 | GTTCAACATGGAAATCCCAGGTAGTTCCTGGTAG |
| P132M9<br>SEQ ID NO: 78 | GGACAACTAATTTGGAGCCAGTTAGCTTCC |
| P132M10<br>SEQ ID NO: 79 | GGAAGCTAACTGGCTCCAAATTAGTTGTCC |
| P132M11<br>SEQ ID NO: 80 | GGAACAAAAAGGAATGGATTCTTGTAGGATCTGG |
| P132M12<br>SEQ ID NO: 81 | CCAGATCCTACAAGAATCCATTCCTTTTTTGTTCC |
| P132M13<br>SEQ ID NO: 82 | CCAATACGCAAATATGGATAACCCGTCTAGGAAC |
| P132M14<br>SEQ ID NO: 83 | GTTCCTAGACGGGTTATCCATATTTGCGTATTGG |
| P132M15<br>SEQ ID NO: 84 | CCAAGGGGAAGTTCTCTGGACTACTATTAAATCCAA<br>AC |
| P132M16<br>SEQ ID NO: 85 | GTTTGGATTTAATAGTAGTCCAGAGAACTTCCCCTT<br>GG |
| P132M17<br>SEQ ID NO: 86 | CAAAAAACTTCACCTTTGGTGGATTGCTAATGATAG<br>C |
| P132M18<br>SEQ ID NO: 87 | GCTATCATTAGCAATCCACCAAAGGTGAAGTTTTTT<br>G |
| P132R<br>SEQ ID NO: 88 | CAATATGTCGACT TATTCCTAAATAGCCCCATAAAG<br>TG |

TABLE 7

The primer sets for point mutation of mhp145.

| Primer | DNA sequence (5' to 3') |
|---|---|
| Mhp145F<br>SEQ ID NO: 89 | GATATAGG ATCCAT AGCTTCAAGGTCGAATACAA<br>CTGC |
| Mhp145M1<br>SEQ ID NO: 90 | AATAATTGCAGAAAAAATTCTTAAAGATCAATGGAA<br>AACAAGTAAATATTCTGATTTTTATTCACAAT |
| Mhp145M2<br>SEQ ID NO: 91 | ATTGTGAATAAAAATCAGAATATTTACTTGTTTTCC<br>ATTGATCTTTAAGAATTTTTTCTGCAATTATT |
| Mhp145R<br>SEQ ID NO: 92 | CAATATGTCGACTTA ATTTACCTTTTGGAGTATCC<br>CATTTTC |

TABLE 8

The primer sets for point mutation of mhp389.

| Primer | DNA sequence (5' to 3') |
|---|---|
| Mhp389F<br>SEQ ID NO: 93 | GATATAGGATCCATGGACAAATTTTCACGAACTG<br>TTCT |
| Mhp389M1<br>SEQ ID NO: 94 | CAATAGTGACAATGGACCCCCCAAATGTTGGTCG |
| Mhp389M2<br>SEQ ID NO: 95 | CGACCAACATTTGGGGGTCCATTGTCACTATTG |
| Mhp389M3<br>SEQ ID NO: 96 | GATAAAGGCGCATCATGGCTTGCGCTTGCACCAAC |
| Mhp389M4<br>SEQ ID NO: 97 | GTTGGTGCAAGCGCAAGCCATGATGCGCCTTTATC |
| Mhp389M5<br>SEQ ID NO: 98 | GGAAAACTTAAAGGTAAATGGACTTTTGGACTAA<br>CCTATTT |
| Mhp389M6<br>SEQ ID NO: 99 | AAATAGGTTAGTCCAAAAGTCCATTTACCTTTAA<br>GTTTTCC |
| Mhp389R<br>SEQ ID NO: 100 | CAATATGTCGACCTAGATTTTAAAGGATTTTTTT<br>AATTCAATAATATAATC |

The method for the point mutation was briefly explained as follows. The chromosome of M. hyopneumoniae PRIT-5 was used as template and DNA fragments was amplified by using the primer sets set forth in the table 3 to table 8 above.

The 50 μL PCR reaction mixture comprised 1×GDP-HiFi PCR buffer, 200 μM of mixture of dATP, dTTP, dGTP, and dCTP, 1 μM of primers, 100 ng of chromosome of M. hyopneumoniae PRIT-5, and 1 U of GDP-HiFi DNA polymerase. The PCR condition was: 5 minutes in 98° C. (one round); 30 seconds in 94° C., 30 seconds in 55° C., X seconds in 68° C. (35 rounds); 5 minutes in 68° C. (one round). Said X was the elongation time for the DNA polymerase and was set depending on the size of the fragment to be amplified. The elongation speed of GDP-HIFI DNA polymerase (GeneDirex, Las Vegas, USA) is 1 kb/15 seconds; therefore, if GDP-HIFI DNA polymerase is used for amplifying a 1 kb DNA fragment, said X shall be set as 15 seconds. After the PCR reaction, an electrophoresis was conducted to verify if the PCR products contained the DNA fragments of expected size. Then, the PCR product was recycled by using a Gel-M™ gel extraction system kit.

Afterward, the PCR product was used as template and amplified by using the primer sets set forth in the table 2 above. The PCR condition was: 2 minutes in 98° C. (one round); 30 seconds in 94° C., 30 seconds in 55° C., X seconds in 68° C. (35 rounds); 5 minutes in 68° C. (one round). Said X was the elongation time for the DNA polymerase and was set depending on the size of the fragment to be amplified. The elongation speed of GDP-HIFI DNA polymerase (GeneDirex, Las Vegas, USA) is 1 kb/15 seconds; therefore, if GDP-HIFI DNA polymerase is used for amplifying a 1 kb DNA fragment, said X shall be set as 15 seconds. After the aforesaid amplification step, a full length sequence of the candidate antigen genes with point mutation can be obtained.

Then, the PCR product was recycled by using a PCR-M™ Clean Up system kit (GeneMark, Taichung, Taiwan) and the cloning thereof was conducted by using a CloneJET PCR Cloning Kit. Colony PCR was conducted to confirm the strains after transformation containing plasmid having the insert DNA and then the plasmids therein were isolated for DNA sequencing (Total Solution Provider of Systems Biology and Chemoinformatics Ltd.). Plasmids containing mutated candidate antigen genes were named as pJET-pdhAM, pJET-xylFM, pJET-P78M, pJET-P132M, pJET-mhp145M, pJET-mhp389M, respectively.

According to the result of sequencing, the DNA sequences of the candidate antigen genes after point mutation were as shown in SEQ ID NO:01 (pdhA), SEQ ID NO:02 (xylF), SEQ ID NO:03 (eutD, was not point-mutated), SEQ ID NO:04 (mhp145), SEQ ID NO:05 (P78 gene), SEQ ID NO:06 (P132 gene), SEQ ID NO:07 (mhp389).

Construction of the Expression Vectors for Expressing the M. hyopneumoniae Antigens In this part of experiments, plasmid pET-MSY was used as backbone for constructing an expression vector for expressing M. hyopneumoniae antigen. pET-MSY is a derivative of pET29a and has a E. coli msyB. Therefore, the expressed recombinant antigen thereby would have a fusion partner MsyB. MsyB is rich in acidic amino acid and is able of increasing the solubility of the protein expressed.

After pJET-eutD, pJET-pdhA, pJET-xylF, pJET-P78, pJET-P132, pJET-mhp145 and pJET-mhp389 being digested by BamHI and SalI, DNA fragment obtained was inserted into pET-Msy digested previously with the same restriction enzymes by ligase. Then, the pET-Msy with the DNA fragment was transformed into E. coli ECOS 9-5. Colony PCR was conducted to confirm the strains after transformation containing plasmid having the insert DNA and then the plasmids therein were isolated for DNA sequencing (Total Solution Provider of Systems Biology and Chemoinformatics Ltd.). Plasmids verified with correct DNA sequence were named as pET-MSYEutD, pET-MSYPdhA, pET-MSYXylF, pET-MSYP78, pET-MSYP132, pET-MSYMhp145, and pET-MSYMhp389, respectively. Those plasmids obtained were examples of the expression vectors for preventing Mycoplasma spp. infection of the present invention.

Expression and Isolation of the M. hyopneumoniae Antigens

The vectors for antigen expression were transformed into E. coli BL21 (DE3). Single colony of consequent strains after transformation was inoculated in LB liquid medium containing kanamycin (working concentration: 30 µg/mL). After culture overnight at 37° C., 180 rpm, the suspension of the bacteria was diluted at ratio of 1:100 and inoculated again in another LB liquid medium containing kanamycin (working concentration: 30 µg/mL). The bacteria were cultured at 37° C., 180 rpm until $OD_{600}$ therefore achieving about 0.6 to 0.8. Then, 0.1 mM of IPTG was added to induce expression. After induction for 4 hours, pellet was collected by centrifugation (10000×g, 10 minutes, 4° C.) and the expression was examined via protein electrophoresis.

Afterward, immobilized-metal affinity chromatography (IMAC) was used for protein isolation through the covalent bonding between the His tag of the N-terminal of the recombinant protein and nickel ions or cobalt ions. The protocol of protein isolation was in accordance with the product description of the QIAexpressionist™ (fourth edition, Qiagen). The pellet was suspended in a lysis buffer (50 mM $NaH_2PO_4$, 300 mM NaCl, 10 mM imidazole, pH 8.0) and disturbed by an ultrasonic processor. After centrifugation (8,000×g, 15 minutes), the supernatant was collected to introduce into a column of 1 mL Ni-NTA resin. The recombinant antigens would adhere on said resin. Then, 15 mL wash buffer (50 mM $NaH_2PO_4$, 300 mM NaCl, 20 mM imidazole, pH 8.0) was introduced into the column to wash the resin so that nonspecific proteins adhering thereon can be removed. Lastly, 20 mL elution buffer was added (50 mM $NaH_2PO_4$, 300 mM NaCl, 250 mM imidazole, pH 8.0) to wash off the recombinant antigens on the resin; wherein the imidazole of high concentration can compete the binding site on the resin with the recombinant proteins and thereby cause the recombinant proteins being washed off. The result of isolation was then examined by protein electrophoresis.

The candidate antigens of the present invention collected by isolation can then be used for the following immune trials to confirm their ability to be used as active ingredient of anti-Mycoplasm spp. subunit vaccines.

Example 3: Swine Immune Challenge Experiments of the Candidate Antigens of the Present Invention In this example, the candidate antigens of the present invention were used as active ingredient for preparing subunit vaccines and tested for immune effects thereof in live swine.

Vaccine Preparation

One isolated recombinant antigen or several isolated recombinant antigens were mixed with alumina gel as an adjuvant to prepare a subunit vaccine or a cocktail subunit vaccine. Every dose of the prepared vaccine was of 2 mL in volume and each kind of antigen contained therein was of 100 µg.

The following table 9 listed the samples prepared in this example for immune challenge experiments.

TABLE 9

Samples of vaccine prepared in Example 3

| Sample | Active Ingredient (Antigen) |
|---|---|
| 1 | PdhA |
| 2 | XylF |
| 3 | EutD |
| 4 | Mhp145 |
| 5 | P78 |
| 6 | P132 |
| 7 | Mhp389 |
| 8 | PdhA + P78 |
| 9 | XylF + Mhp145 |

The swine immune challenge experiments would be conducted by using Bayovac® MH-PRIT-5 (made by using M. hyopneumoniae PRIT-5, as a positive control group), subunit vaccines (samples 1-7 of the present invention), and cocktail vaccines (samples 8 and 9 of the present invention).

33 SPF pigs of 4-week old were brought from Agricultural Technology Research Institute and fed with same feed, environment, and growth condition in piggery before experiments.

After the pigs were fed to 35-day and 49-day old, the pigs were administrated 2 mL of vaccine above via intramuscular injection.

Challenge Experiments

The aforesaid pigs being induced immune response were challenged by Mycoplasm spp. at 109-day old to confirm the immune effect of the aforesaid vaccines.

First of all, a lung collected from pigs infected by Mycoplasm spp. was ground in 20 mL of Friis medium and centrifugated at 148.8×g for 10 minutes. The supernatant was removed to a clean tube and centrifugated again at 7,870×g for 40 minutes. Then, the supernatant was discarded and the precipitation was suspended in 6 mL of Friis medium to obtain a suspension. Afterward, the suspension was filtered by membrane of 5 μm and 0.45 μm sequentially to obtain bacteria solutions required for the challenge experiments.

Figure 4:
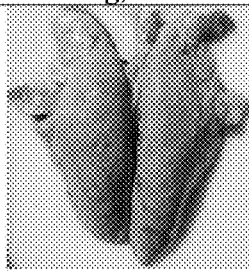
FIG. 4 shows the records of the challenge experiments conducted in the $3^{rd}$ example of the present invention.
Figure 4:
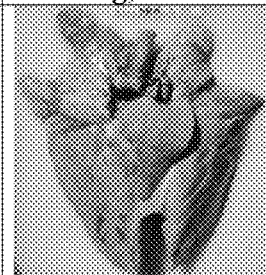
Figure 4:
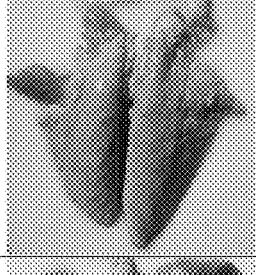
Figure 4:
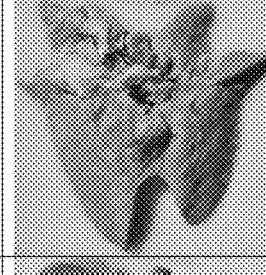
Figure 4:
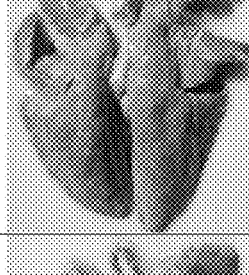
Figure 4:
Figure 4:
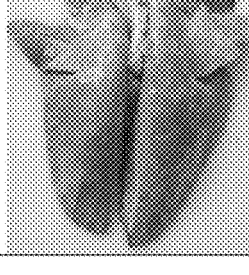
Figure 4:
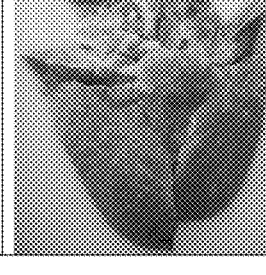
Figure 4:
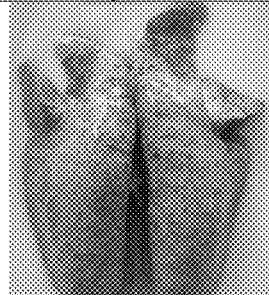
Figure 4:
Figure 4:
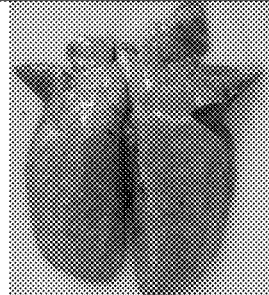
Figure 4:
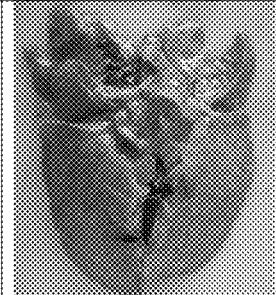
Figure 4:
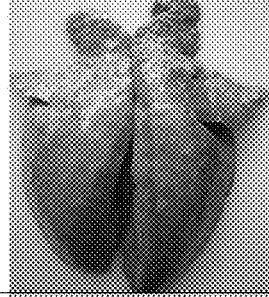
Figure 4:
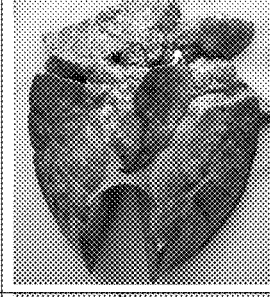
Figure 4:
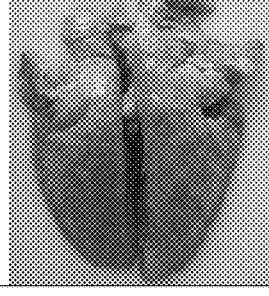
Figure 4:
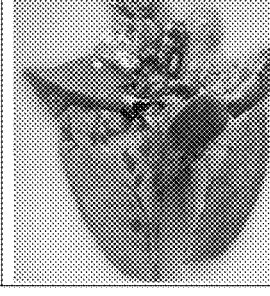
Figure 4:
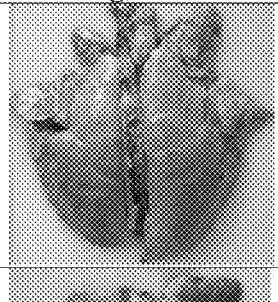
Figure 4:
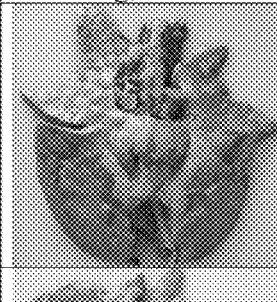
Figure 4:
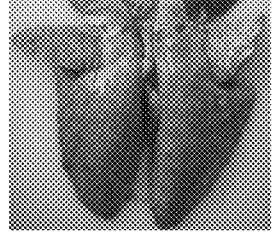
Figure 4:
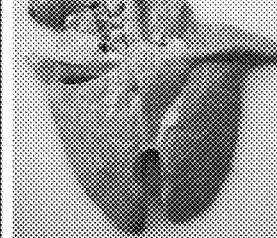
Figure 4:
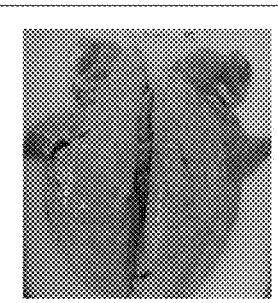
Figure 4:
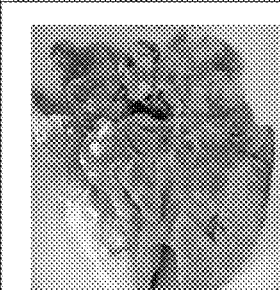

The bacteria solution (5 mL) was administrated to narcotized pigs via trachea thereof. After 28 days from administration, the pigs were sacrificed and dissected to collect lung thereof. The immune effect was examined by observing the lung and recorded according to the following criteria: any of meddle upper lobes and upper lobes of any side of the lung observed of pathological trait was scored as 10 points; any of meddle upper lobe and diaphragmatic lobes of any side of the lung observed of pathological trait was scored as 5 points. The full score was 55 points. The observation records were shown in FIG. 4.

In comparison with the results of non-injected pigs, the seven candidate antigens of the present invention were able to provide equivalent immune effects as conventional vaccine (Bayovac® MH-PRIT-5). If the higher safety of subunit vaccines is taking into consideration, the vaccines containing the candidate antigens of the present invention shall be valued more.

On the other hand, it was not common to use two or more antigens that would induce immune effects in one vaccine because the two or more antigens may not provide doubled immune effect. In fact, there is higher chance that the two or more antigens may interfere or against each other and consequently reduce the immune effect of the vaccine. According to the result of this example, sample 8 and sample 9 of the present invention (i.e. cocktail vaccine) unexpectedly provide significant increase in the immune effect. That said, the subunit vaccines of the present invention not only have high safety but also provide better immune effect when the candidate antigens of the present invention are used in combination.

Those having ordinary skill in the art can readily understand any possible modifications based on the disclosure of the present invention without apart from the spirit of the present invention. Therefore, the examples above shall not be used for limiting the present invention but intend to cover any possible modifications under the spirit and scope of the present invention according to the claims recited hereinafter.

---

What is claimed is:

1. A composition for preventing a disease caused by *Mycoplasma* spp., comprising:

an active ingredient, comprising a protein of Mhp389; and a pharmaceutically acceptable adjuvant;

wherein said Mhp389 comprises the sequence of SEQ ID NO: 14.

2. The composition of claim 1, wherein said active ingredient is of a concentration of 50 to 3500 μg/mL based on the total volume of said composition.

3. The composition of claim 1, wherein said pharmaceutically acceptable adjuvant is a complete Freund's adjuvant, an incomplete Freund's adjuvant, an alumina gel, a surfactant, a polyanion adjuvant, a peptide, an oil emulsion, or a combination thereof.

4. The composition of claim 1, further comprising a pharmaceutically acceptable additive.

5. The composition of claim 4, wherein said pharmaceutically acceptable additive is a solvent, a stabilizer, a diluent, a preservative, an antibacterial agent, an antifungal agent, an isotonic agent, a absorption delaying agent, or a combination thereof.

* * * * *